US012774777B2

(12) United States Patent
Stalter et al.

(10) Patent No.: US 12,774,777 B2
(45) Date of Patent: Oct. 27, 2026

(54) POSITIONER SYSTEM FOR ULTRASOUND PROBE

(71) Applicant: GE Precision Healthcare LLC, Waukesha, WI (US)

(72) Inventors: Ross Stalter, Hartland, WI (US); Robert Andrew Meurer, Waukesha, WI (US); Adam Gregory Pautsch, Oconomowoc, WI (US); Sihem Lazizi, Cannes (FR); Lin Koop, Glendale, WI (US)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 0 days.

(21) Appl. No.: 19/045,220

(22) Filed: Feb. 4, 2025

(65) Prior Publication Data

US 2026/0227027 A1 Aug. 6, 2026

(51) Int. Cl.

| | |
|---|---|
| ***F16M 11/20*** | (2006.01) |
| ***A61N 7/00*** | (2006.01) |
| ***F16M 11/04*** | (2006.01) |
| ***F16M 11/08*** | (2006.01) |
| ***F16M 11/28*** | (2006.01) |

(52) U.S. Cl.

CPC ........... *F16M 11/2035* (2013.01); *A61N 7/00* (2013.01); *F16M 11/041* (2013.01); *F16M 11/08* (2013.01); *F16M 11/2085* (2013.01); *F16M 11/28* (2013.01); *A61N 2007/0026* (2013.01)

(58) Field of Classification Search

CPC .. F16M 11/2035; F16M 11/041; F16M 11/08; F16M 11/2085; F16M 11/28; A61N 7/00; A61N 2007/0026

See application file for complete search history.

(56) References Cited

U.S. PATENT DOCUMENTS

| | | | | |
|---|---|---|---|---|
| 2,599,269 A * | 6/1952 | Markle .............. | F16M 11/2064 | 248/404 |
| 2,669,958 A * | 2/1954 | Sweeney ............ | B23K 37/0426 | 269/45 |
| 3,891,301 A * | 6/1975 | Heller .................... | F16M 11/08 | 396/428 |
| 4,183,511 A * | 1/1980 | Marek ..................... | B66C 23/48 | 269/71 |

(Continued)

FOREIGN PATENT DOCUMENTS

| | | |
|---|---|---|
| CN | 107280739 A | 10/2017 |
| CN | 206729905 U | 12/2017 |

(Continued)

*Primary Examiner* — Eret C Mcnichols

(74) *Attorney, Agent, or Firm* — Fletcher Yoder, P.C.

(57) ABSTRACT

Embodiments of the present disclosure relate to a positioner system for use with an ultrasound probe to treat a subject via neuromodulation, and the techniques for using the same. In certain embodiments, the positioner system may include a receptacle for receiving the ultrasound probe, a pressure applicator to apply a steady pressure to maintain a position of ultrasound probe against the patient's skin, and a slider arm to extend near or above the subject and support the pressure applicator and probe holder. The positioner system may include multiple degrees of freedom to accommodate a subject's clinical needs and/or treatment protocol that utilizes the ultrasound probe.

13 Claims, 12 Drawing Sheets

(56) References Cited

U.S. PATENT DOCUMENTS

| | | | | |
|---|---|---|---|---|
| 4,671,478 | A * | 6/1987 | Schoenig | F16M 11/245 248/123.2 |
| 4,863,133 | A * | 9/1989 | Bonnell | F16M 11/14 403/56 |
| 4,949,944 | A * | 8/1990 | Groff, Sr. | B25B 5/003 269/45 |
| 4,987,817 | A * | 1/1991 | Diaz | G10D 13/28 84/421 |
| 5,632,459 | A * | 5/1997 | Brett | F16M 11/2092 248/168 |
| 5,640,781 | A * | 6/1997 | Carson | A45D 20/16 132/229 |
| 5,704,900 | A * | 1/1998 | Dobrovolny | A61B 17/0281 600/235 |
| 5,824,007 | A * | 10/1998 | Faraz | F16M 11/046 600/102 |
| 6,007,032 | A * | 12/1999 | Kuo | F16M 11/16 248/188.7 |
| 6,129,319 | A * | 10/2000 | Metelski | G02B 7/001 359/384 |
| 6,390,424 | B1 * | 5/2002 | Kidushim | F16M 11/24 248/404 |
| 6,796,536 | B1 * | 9/2004 | Sevier, IV | A47B 23/046 248/924 |
| 7,434,772 | B1 * | 10/2008 | Jou | A45D 20/14 248/124.2 |
| 7,514,619 | B1 * | 4/2009 | Bruce | A47B 81/00 248/463 |
| 8,083,196 | B2 * | 12/2011 | Chang | A61B 90/50 248/278.1 |
| 9,320,494 | B2 * | 4/2016 | Strong | A61B 8/0841 |
| 9,366,378 | B2 * | 6/2016 | Schmidt | F16M 11/04 |
| 9,532,837 | B2 * | 1/2017 | Singh | A61B 90/10 |
| 9,719,627 | B2 * | 8/2017 | Hennessey | F16M 11/2021 |
| 10,004,569 | B2 * | 6/2018 | Singh | A61B 90/57 |
| 10,744,526 | B2 * | 8/2020 | Johnson | B25H 1/00 |
| 11,253,645 | B2 * | 2/2022 | Avalos | A61K 9/0085 |
| 11,388,497 | B1 * | 7/2022 | Kuo | F16B 2/10 |
| 11,413,009 | B2 | 8/2022 | Rijken et al. | |
| 11,771,386 | B2 | 10/2023 | Tang et al. | |
| 11,774,038 | B2 * | 10/2023 | West | F16B 7/0493 248/276.1 |
| 12,516,769 | B1 * | 1/2026 | Breed | F16M 11/2014 |
| 2002/0074463 | A1 * | 6/2002 | Nakamura | A61B 90/50 248/127 |
| 2005/0193451 | A1 * | 9/2005 | Quistgaard | A61B 34/76 901/9 |
| 2005/0267368 | A1 | 12/2005 | Boctor et al. | |
| 2006/0089626 | A1 | 4/2006 | Megele et al. | |
| 2006/0120550 | A1 * | 6/2006 | McCann | H04R 1/08 381/366 |
| 2007/0060818 | A1 | 3/2007 | Ilkubo et al. | |
| 2007/0129634 | A1 | 6/2007 | Hickey et al. | |
| 2009/0099487 | A1 | 4/2009 | Chaluisan et al. | |
| 2009/0230269 | A1 * | 9/2009 | Dallarosa | F16M 11/12 248/299.1 |
| 2010/0204578 | A1 * | 8/2010 | Schmidt | A61B 8/4281 600/443 |
| 2018/0161114 | A1 | 6/2018 | Bax et al. | |
| 2022/0087711 | A1 | 3/2022 | Piron et al. | |

FOREIGN PATENT DOCUMENTS

| | | | |
|---|---|---|---|
| JP | 5410003 | B2 | 2/2014 |
| WO | WO-8402834 | A * | 8/1984 |
| WO | 2006040309 | A1 | 4/2006 |
| WO | 2014077439 | A1 | 5/2014 |

* cited by examiner

POSITIONER SYSTEM FOR ULTRASOUND PROBE

FIELD OF THE TECHNOLOGY DISCLOSED

The subject matter disclosed herein relates to techniques to support identifying, targeting, and/or dosing regions of interest in a subject via application of energy (e.g., neuromodulating ultrasound energy) to cause targeted physiological outcomes. In particular, the disclosed techniques may facilitate the accurate delivery of a therapeutic dose of ultrasound energy to a target region for a sustained period of time (e.g., throughout duration of treatment).

BACKGROUND

Ultrasound-based neuromodulation has been used to treat a variety of clinical conditions. However, the targeting of specific tissue for neuromodulation may be challenging. For example, certain patients may have variations in organ size or location relative to other patients based on their height, weight, age, gender, clinical condition, and the like, which may impact targeting and dose delivery using various neuromodulation techniques. Further, the effectiveness of ultrasound-based neuromodulation may be dependent on precise and accurate positioning of an energy application device (e.g., ultrasound probe) for an extended period of time (e.g., throughout treatment).

BRIEF DESCRIPTION

Certain embodiments commensurate in scope with the claimed subject matter are summarized below. These embodiments are not intended to limit the scope of the claimed subject matter, but rather these embodiments are intended to only provide a brief summary of possible embodiments. Indeed, the disclosure may encompass a variety of forms that may be similar or different from the embodiments set forth below.

In one embodiment, an ultrasound probe positioner system is provided. The ultrasound probe positioner system includes a probe holder having a receptacle configured to receive an ultrasound probe. Further, the ultrasound probe positioner system includes a pressure applicator. The pressure applicator includes a pivot arm configured to rotatably couple to the receptacle of the probe holder. Additionally, the pressure applicator includes a first knob, where rotation of the first knob in a first direction is configured to prevent relative motion between the pivot arm and the receptacle of the probe holder, and a second knob, where rotation of the second knob is configured to adjustably apply pressure to the pivot arm and control an angular position of the pivot arm. Moreover, the ultrasound probe positioner system includes a slider arm having an arm and a slide disposed on the arm, where the slide is configured to couple to the pressure applicator, and where a position of the slide is adjustable along a length of the arm.

In one embodiment, a method is provided that includes the steps of acquiring image data of a subject using an ultrasound probe, identifying a region of interest based on the acquired image data, determining a treatment position on the skin of the subject based on the region of interest, and positioning an ultrasound probe on or over the treatment position. Further, the method includes affixing a probe holder of a positioner system over the ultrasound probe, rotating a first knob of the positioner system in a first direction to prevent relative motion between components of the positioner system, rotating a second knob of the positioner system to rotate a pivot arm of the positioner system into the subject such that the ultrasound probe is pressed against the treatment position with steady pressure, and administering a therapy dose of ultrasound energy from the ultrasound probe through the subject's skin to the region of interest.

In one embodiment, a neuromodulation energy application system is provided. The neuromodulation energy application system includes an ultrasound probe configured to apply neuromodulating energy through a portion of a subject's skin to a region of interest of an internal tissue. Additionally, the neuromodulation energy application system includes a positioner system having a probe holder configured to removably couple to the ultrasound probe, and a pressure applicator with a pivot arm configured to couple to the probe holder. The pressure applicator is configured to rotate the pivot arm in a direction towards the subject's skin and apply a steady pressure to maintain a position of the ultrasound probe against the subject's skin. Further, the positioner system includes a slider arm configured to extend near or above the subject. The slider arm includes a slide mechanism configured to couple to the pressure applicator, where the slide mechanism is configured to adjust a position of the pressure applicator along a length of the slider arm.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
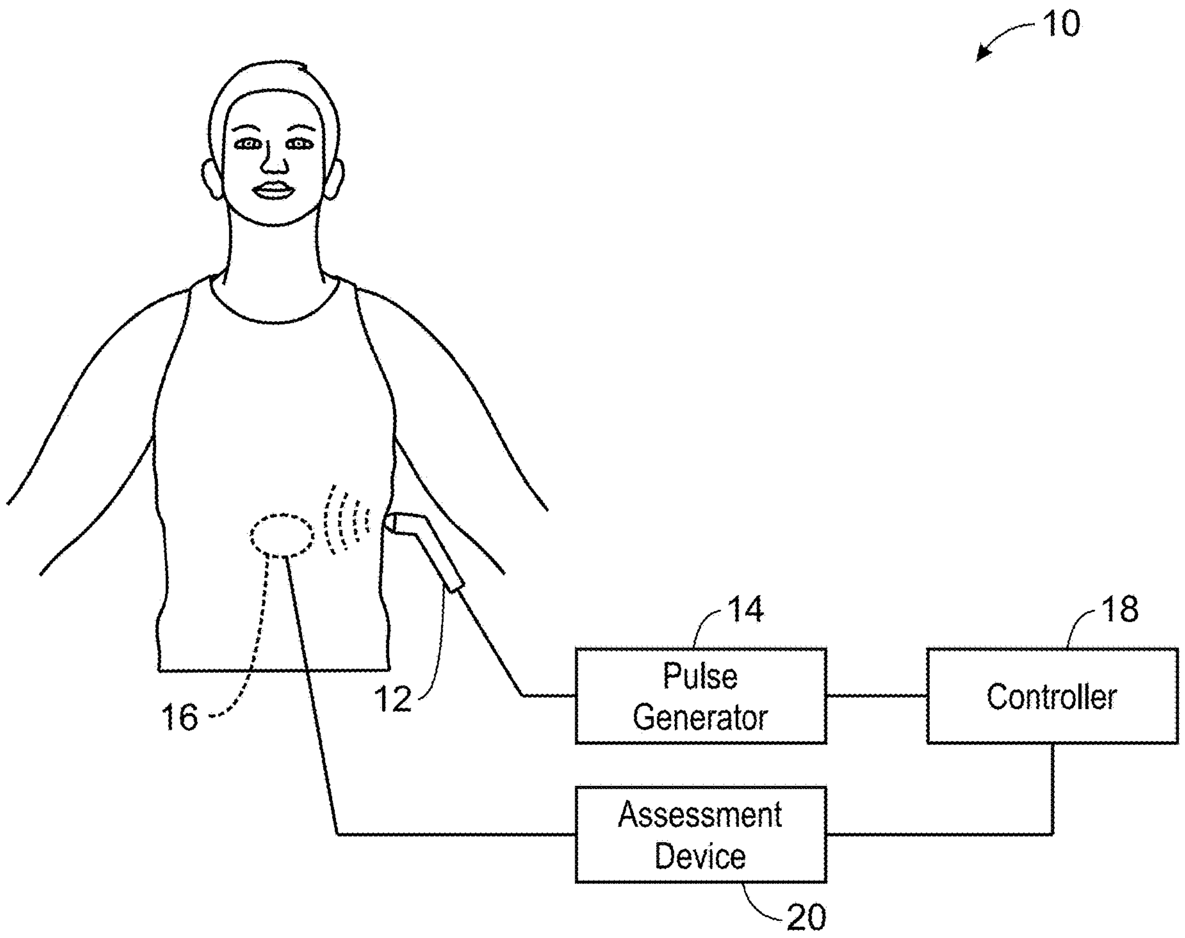
FIG. 1 is a schematic representation of a neuromodulation system according to embodiments of the present disclosure.

One or more specific embodiments are described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Any examples or illustrations given herein are not to be regarded in any way as restrictions on, limits to, or express definitions of, any term or terms with which they are utilized. Instead, these examples or illustrations are to be regarded as being described with respect to various particular embodiments and as illustrative only. Those of ordinary skill in the art will appreciate that any term or terms with which these examples or illustrations are utilized will encompass other embodiments that may or may not be given therewith or elsewhere in the specification and all such embodiments are intended to be included within the scope of that term or terms. Language designating such non-limiting examples and illustrations includes, but is not limited to, "for example", "for instance", "such as", "e.g.", "including", "in certain embodiments", "in some embodiments", and "in one (an) embodiment." All numerical values within the detailed description herein are modified by "about" the indicated value, and take into account experimental error and variations, manufacturing tolerances or constraints, and so forth that would be expected by a person having ordinary skill in the art. For example, "about" or "approximately" may refer to ±0.5%, ±1%, ±2, ±5%, ±10%, or ±15%.

When introducing elements of various embodiments of the present disclosure, the articles "a", "an", "the", and "said" are intended to mean that there are one or more of the elements. The terms "comprising", "including", and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

As mentioned above, ultrasound-based neuromodulation may be used to treat a variety of clinical conditions, including metabolic disorders, such as diabetes or hyperglycemia, inflammation or immune disorders, and so forth. In practice, an energy application device (e.g., a therapy probe, an ultrasound therapy probe) may be positioned on a patient's skin to deliver neuromodulating energy through the skin to a region of interest to achieve target physiological outcomes. However, identifying and targeting a specific region of interest (e.g., tissue) for neuromodulation may be challenging. For example, each patient's treatment may be personalized and vary from patient-to-patient according to variations in anatomy (e.g., organ location, body mass index (BMI), etc.), clinical condition of the patient, and responsiveness of the patient to neuromodulation. Accordingly, an effective energy application site for neuromodulating a region of interest may be at one site for one patient and a slightly different site for another patient. Such sites may include areas on the patient's back or side, as well as areas that are difficult to position a therapy probe, such as under the lower edge of a patient's rib cage and/or between two ribs. Additionally, effectively identifying a region of interest and applying energy to the region of interest may involve applying substantial pressure or force (e.g., in a range of 1-15 pounds-force) to press inward against and maintain the imaging and/or energy application device (e.g., ultrasound probe) in contact with the patient's skin, as the region of interest may be at a significant depth beneath the surface of the patient's skin (e.g., in a range of 1-10 centimeter, 9-15 centimeters, 10-20 centimeters, etc.). Further, treatment may include applying neuromodulation energy at a specific site for an extended period of time (e.g., 30 minutes, 1 hour, etc.) in order to achieve a desired physiological outcome. Therefore, human operators (e.g., clinicians, sonographers, etc.) may be unable to hold (e.g., steady, at the proper angle and/or orientation) an ultrasound probe at the treatment site throughout the duration of treatment and may be unable to apply sufficient pressure for effective treatment.

Accordingly, the present disclosure is directed towards neuromodulation techniques utilizing an ultrasound probe positioner system. The ultrasound probe positioner system may, in certain implementations, include a probe holder, a pressure applicator, and a slider arm. The probe holder may include a receptacle to receive and support an ultrasound probe or other suitable energy application and/or imaging device. The pressure applicator may include a pivot arm to rotatably couple to the probe holder (e.g., via a ball joint at an end of the pivot arm), and a worm gear system operated by two knobs, a positioner lock knob (e.g., a first knob) and a compression adjustment knob (e.g., a second knob). The worm gear system may be operated to rotate the pivot arm in a direction towards or away from the subject, thereby bringing the ultrasound probe against a patient's skin with steady and gradual pressure. The pressure applicator may be coupled to the slider arm via a slide mechanism that may adjust a position of the pressure applicator along the length of the slider arm. The slider arm may be a cantilever arm with a mount on one end to couple to a cart, a mobile stand, an operating table, a bed, a neuromodulation system controller, a wearable device, or any other suitable support structure. In this way, the slider arm may extend above or near a patient while supporting the pressure applicator and probe holder (via the pressure applicator). Additionally, the slider arm may include a cord management feature on the free end of the arm (e.g., on the end opposite the mount) to accommodate a cord of the ultrasound probe. During operation, the cord of the ultrasound probe (e.g., a cord configured to transport ultrasound signals, control signals, power signals, or a combination thereof) may extend through an opening in the receptacle of the probe holder, to be inserted into the cord management feature, thereby reducing the cable weight on the ultrasound probe and preventing the cord from hanging or resting on the subject (e.g., patient) or operator (e.g., sonographer). The cord management feature may also prevent the slide mechanism from sliding off the free end of the slider arm. In some embodiments, the slider arm may have one or more features to limit or prevent free radial rotation of the slider arm during operation (e.g., a hexagonal cross section, a slot or flat spot on a surface, etc.).

During operation, an operator may "free scan" with the ultrasound probe (e.g., use the probe while it is disconnected from the positioner system) to gather image data of a subject to determine a treatment position of the ultrasound probe associated with a region of interest for neuromodulation. Once the treatment position is identified, the operator may bring the probe holder of the positioner system to the ultrasound probe by rotating the slider arm to extend above or near the subject, adjusting a position of the pressure applicator along the slider arm via the slide mechanism, rotating the pivot arm of the pressure applicator, or a combination thereof. The ultrasound probe may then be inserted into the receptacle of the probe holder.

In some embodiments, the receptacle is a two-piece assembly including a lower receptacle to couple to the probe and an upper receptacle to couple to the positioner system (e.g., the pressure applicator). For example, the upper receptacle may rotatably couple to the pivot arm of the pressure applicator. The lower receptacle may include one or more walls formed to substantially match the profile (e.g., shape and curvature) of a portion of the ultrasound probe, such that the ultrasound probe substantially retains its profile when inserted into the lower receptacle (e.g., has substantially the same hand feeling when held by the operator). Mating ends of the upper receptacle and the lower receptacle may include interfacing teeth to allow for small relative motion (e.g., rotation) between the upper receptacle and the lower receptacle, thus allowing for minor or fine (e.g., millimeter) adjustments of the position of the probe after it is inserted into the lower receptacle.

Once the probe is in the treatment position and coupled to the positioner system (e.g., via the probe holder), the operator may rotate the positioner lock knob of the pressure applicator in a first direction (e.g., clockwise) to prevent relative motion between the probe holder and the pivot arm and prevent relative motion of the pressure applicator along the slider arm via the slide mechanism. Next, the operator may rotate the compression adjustment knob (e.g., a second knob) to rotate the pivot arm into the subject, thereby pressing the ultrasound probe against the treatment position with steady pressure. When pressure is applied to the ultrasound probe (e.g., via rotation of the compression adjustment knob), the interfacing teeth of the probe holder (e.g., on mating ends of the upper receptacle and the lower receptacle) may interlock, thus preventing any further movement of the ultrasound probe. Accordingly, the positioner system may lock the ultrasound probe into position against the patient's skin with a desired amount of pressure for the duration of treatment (e.g., 30 minutes, 1 hour, etc.). After the treatment (e.g., neuromodulation energy) is administered via the ultrasound probe to the region of interest, the operator may rotate the positioner lock knob in a second direction (e.g., counterclockwise) to release the pressure and allow motion between components of the positioner system.

Therefore, the disclosed techniques may increase the effectiveness (e.g., due to proper and consistent probe placement and pressure) and reduce the complexity of administering neuromodulation treatments. For example, operators may not have to learn different techniques for identifying a region of interest and associated treatment position with the positioner system, as the positioner system allows for "free scanning" before the ultrasound probe is inserted into the probe holder. Further, the positioner system may be operated by a single operator using a single hand, as rotating two knobs sequentially may secure the position of the ultrasound probe (e.g., prevent movement between components of the system) and apply pressure, and rotating a single knob of the two knobs may release the pressure applied and allow movement between components of the system. Moreover, the worm gear system of the pressure applicator may allow for gradual and steady pressure application, thereby preventing or reducing large and sudden changes in applied pressure which may lead to patient discomfort. Additionally, the worm gear system may prevent backlash between components of the positioner system during pressure application and pressure release. The positioner system may also reduce the time needed to set up and adjust the system to the subject's unique anatomy and clinical condition, as the positioner system includes multiple degrees of freedom allowing for height adjustments, rotational adjustments, and the like. Additionally, the positioner system may reduce the time in between treating patients, as the ultrasound probe may be the only component of the neuromodulation system to directly contact the patient's skin during treatment, and thus the only component that requires cleaning and disinfecting in between uses. Likewise, the positioner system is not required to be machined out of biosafe and biocompatible materials, as it is not expected to contact the subject's skin, which may reduce the cost of manufacturing the positioner system. Accordingly, the presently disclosed techniques may improve the experience of both patients and operators (e.g., clinicians, sonographers, etc.) during neuromodulation treatments.

With the foregoing in mind, FIG. 1 is a schematic representation of a system 10 for neuromodulation. While the depicted elements of the system 10 are shown separately, it should be understood that some or all of the elements may be combined with one another. Further, some or all of the elements may communicate in a wired or wireless manner with one another.

The neuromodulation system 10 may be used to achieve neurotransmitter release and/or activate components (e.g., the presynaptic cell, the postsynaptic cell) of a synapse in response to an application of energy (e.g., ultrasound energy). The illustrated system 10 includes an energy application device 12 (e.g., an ultrasound therapy probe) coupled to a pulse generator 14. In certain embodiments, the pulse generator 14 may be an extracorporeal device, e.g., may operate to apply energy transdermally or in a noninvasive manner from a position outside of a subject's body. The energy application device 12 is configured to receive energy pulses from the pulse generator 14, e.g., via leads or wireless connection. During operation, the energy pulses are directed to a region of interest 16 of an internal tissue or organ of a subject (e.g., a peripheral tissue), which in turn results in a targeted physiological outcome. The target physiological outcome may include a local and/or systemic change in concentration of a biologically active molecule, process, or function. For example, during a metabolic disorder treatment, the applied energy pulses may result in changes to a concentration of a glucose transporter pathway molecule and/or an incretin pathway molecule.

In certain embodiments, the energy application device 12 and/or the pulse generator 14 may communicate wirelessly, for example with a controller 18 that may in turn provide instructions to the pulse generator 14. In other embodiments, the pulse generator 14 may be integrated within the controller 18. In embodiments in which the pulse generator 14 is extracorporeal, the energy application device 12 may be operated by a caregiver (e.g., sonographer) and positioned at a spot on or above a subject's skin such that the energy pulses are delivered transdermally to a desired internal tissue (e.g., a peripheral tissue that includes one or more peripheral axon terminals). Once the energy application device 12 is positioned to apply energy pulses to the desired site (e.g., region of interest 16), the system 10 may initiate neuromodulation of one or more target internal sites (e.g., one or more nerve pathways) to achieve a targeted physiological outcome or clinical effect(s), such as treatment of a metabolic disorder.

In certain embodiments, the system 10 may include an assessment device 20 coupled to the controller 18. The assessment device 20 may assess characteristics that are indicative of whether the targeted physiological outcome(s) of the neuromodulation have been achieved. In one embodiment, the target physiological outcome and/or characteristics may be local. For example, the modulation (e.g., of one or more nerve pathways) may result in local tissue or function changes, such as tissue structure changes, local change of concentration of certain molecules, tissue displacement, increased fluid movement, and the like. The targeted physiological outcome may be a goal of the treatment. For example, the targeted physiological outcome may include hormone secretion (such as secretion of insulin from the pancreas or ghrelin from the GI), cell viability, and/or cell or hormonal stability.

Additionally, or alternatively, the modulation may result in a systemic or non-local changes, and the targeted physiological outcome may be related to a change in concentration of circulating molecules or a change in a characteristic of a tissue that does not include the region of interest 16 to which energy was directly applied. In one example, the displacement may be a proxy measurement for a desired modulation, and displacement measurements below an expected displacement value may result in modification of modulation parameters until an expected displacement value is induced. Accordingly, the assessment device 20 may be configured to assess concentration changes of a molecule or molecules of interest in some embodiments. In certain embodiments, the assessment device 20 may be an imaging device configured to assess changes in organ size and/or position, as well as changes in tissue characteristics. In some embodiments, the assessment device 20 monitors changes in blood pressure, indicative of arterial resistivity changes associated with treatment. In another embodiment, the assessment device 20 may be a circulating glucose monitor. Further, in another embodiment, the assessment device 20 may assess local temperature rises of tissue, which may be detected using a separate temperature sensor or ultrasound imaging data from the energy application device 12. Assessment of speed of sound differences may be detected through difference imagine techniques pre/during/post therapy.

Based on the assessment from the assessment device 20, the modulation parameters of the controller 18 may be altered such that an effective amount of energy is applied. For example, if a desired modulation is associated with a change in concentration of a molecule of interest (e.g., circulating concentration or tissue concentration of one or more molecules) within a defined time window (e.g., 5 minutes, 30 minutes after a procedure of energy application starts) or relative to a baseline measurement at the start or before initiation of a procedure, a change of the modulation parameters such as pulse frequency or other parameters may be desired, which in turn may be provided to the controller 18. The desired change in modulation parameters may be provided to the controller either by an operator or via an automatic feedback loop, for defining or adjusting the energy application parameters or modulation parameters of the pulse generator 14 until the modulation parameters result in an effective amount of energy being applied.

The system 10 as provided herein may provide energy pulses according to various modulation parameters. For example, the modulation parameters may include various stimulation time patterns, ranging from continuous to intermittent. With intermittent simulation, energy is delivered for a period of time at a certain frequency during a signal-on time. The signal-on time is followed by a period of time with no energy delivery, referred to as signal-off time. The modulation parameters may also include frequency and duration of a stimulation application. The application frequency may be delivered at various time periods, for example, within a day or week. The treatment duration may last for various time periods, including but not limited to, from a few minutes to several hours. In certain embodiments, treatment duration with a specified stimulation pattern may last for one hour, repeated at, e.g., 72-hour intervals. In certain embodiments, treatment may be delivered at a higher frequency, say every three hours, for shorter durations, for example, 30 minutes. The application of energy, in accordance with modulation parameters, such as treatment duration and frequency, may be adjustably controlled to achieve a desired result.

Figure 2:
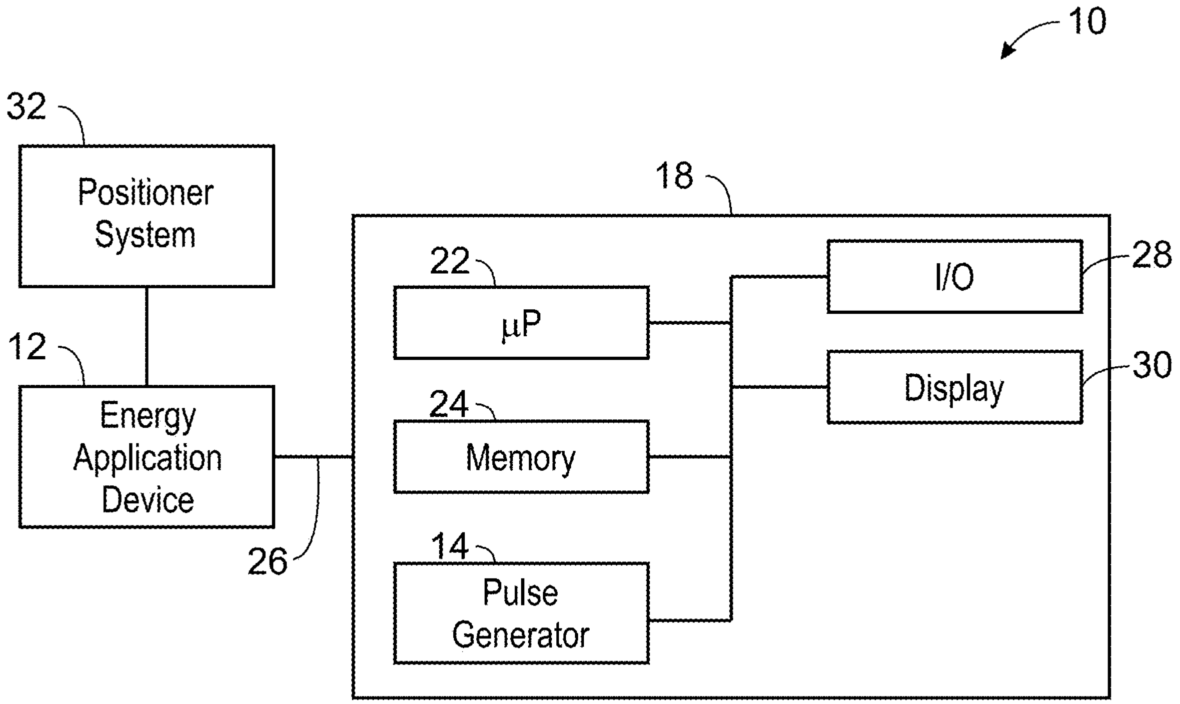
FIG. 2 is a block diagram a neuromodulation system according to embodiments of the present disclosure.

FIG. 2 is a block diagram of certain components of the system 10. As provided herein, the system 10 for neuromodulation may include a pulse generator 14 that is adapted to generate a plurality of energy pulses for application to a tissue of a subject. The pulse generator 14 may be separate or may be integrated into an external device, such as the controller 18. The controller 18 includes a processor 22 for controlling the device. Software code or instructions are stored in the memory 24 of the controller 18 for execution by the processor 22 to control the various components of the device (e.g., pulse generator 14, etc.). The controller 18 and/or the pulse generator 14 may be connected to the energy application device 12 via one or more leads 26 or wirelessly.

The controller 18 also includes a user interface with input/output (I/O) circuitry 28 and a display 30 that are adapted to let a clinician provide selection inputs or modulation parameters to modulation programs. Each modulation program may include one or more sets of modulation parameters including pulse amplitude, pulse width, pulse frequency, etc. The pulse generator 14 modifies its internal parameters in response to the control signals from the controller 18 to vary the stimulation characteristics of energy pulses transmitted through lead 26 to a subject to which the energy application device 12 is applied. Any suitable type of pulse generating circuitry may be employed, including but not limited to, constant current, constant voltage, multiple-independent current or voltage sources, etc. The energy applied is a function of the current amplitude and pulse width duration. The controller 18 permits adjustably controlling the energy by changing the modulation parameters and/or initiating energy application at certain times or cancelling/suppressing energy application at certain times.

In one embodiment, the adjustable control of the energy application device 12 is based on information about the concentration of one or more molecules in the subject (e.g., a circulating molecule). If the information is from the assessment device 20, a feedback loop may drive the adjustable control. For example, if a circulating glucose concentration in blood or urine of the subject, as measured by the assessment device 20, is above a predetermined threshold or range, the controller 18 may initiate energy application to a region of interest (e.g., liver) with modulation parameters that are associated with a reduction in circulating glucose. The initiation of energy application (e.g., treatment) may be triggered by the glucose concentration drifting above a predetermined (e.g., desired) threshold or outside a predefined range. In another embodiment, the adjustable control may be in the form of altering modulation parameters when an initial application of energy does not result in an expected change in a target physiological outcome (e.g., concentration of a molecule of interest) within a predefined time frame (e.g., 1 hour, 2 hours, 4 hours, 1 day, etc.).

In one embodiment, the memory 24 stores different operating modes that are selectable by the operator. For example, the stored operating modes may include instructions for executing a set of modulation parameters associated with a particular treatment site, such as regions of interest in the liver, pancreas, gastrointestinal tract, spleen, and the like. Different sites may have different associated modulation parameters. Rather than having the operator manually input the modes, the controller 18 may be configured to execute the appropriate instruction based on the selection of the operator.

In another embodiment, the memory 24 stores operating modes for different types of procedures or treatment. For example, activation may be associated with a different stimulating pressure or frequency range relative to those associated with depressing or blocking tissue function. In a specific example, when the energy application device 12 is an ultrasound transducer, the time-averaged power (temporal average intensity) and peak positive pressure are in the range of 1 $mW/cm^2$-30,000 $mW/cm^2$ (temporal average intensity) and 0.1 MPa to 7 MPa (peak pressure). In one example, the temporal average intensity is less than 35 $W/cm^2$ in the region of interest to avoid levels associated with thermal damage and ablation/cavitation. In another specific example, when the energy application device 12 is a mechanical actuator, the amplitude of vibration is in the range of 0.1 to 10 mm. The selected frequencies may depend on the mode of energy application (e.g., ultrasound or mechanical actuation). The controller 18 may be capable of operating in a validating mode to acquire a treatment position, and the treatment position may be implemented as part of a treatment operating mode that executes a treatment protocol (e.g., energy application) when the energy application device 12 is positioned at the treatment position. In another embodiment, the memory 24 stores a calibration or setting mode that permits adjustment or modification of the modulation parameters to achieve a desired result. In one example, the stimulation starts at a lower energy parameter and increases incrementally, either automatically or upon receipt of an operator input. In this manner, the operator may achieve tuning of the induced effects as the modulation parameters are being changed.

The system 10 may also include an imaging device that facilitates focusing the energy application device 12. In one embodiment, the imaging device may be integrated with or the same device as the energy application device 12 such that different ultrasound parameters (frequency, aperture, or energy) are applied for selecting (e.g., spatially selecting) a region of interest and for focusing energy to the selected region of interest for targeting and subsequent neuromodulation. In another embodiment, the memory 24 stores one or more targeting or focusing modes that is used to spatially select the region of interest within an organ or tissue structure. Spatial selection may include selecting a subregion of an organ to identify a volume of the organ that corresponds to a region of interest. Spatial selection may rely on image data as provided herein. Based on the spatial selection, the energy application device 12 may be focused on the selected volume corresponding to the region of interest. For example, the energy application device 12 may be configured to first operate in the targeting mode and/or the validating mode to capture image data to be used for identifying the region of interested and associated treatment position (e.g., a position of the energy application device 12 configured to apply energy to the area of interest). The targeting mode and/or validating mode energy is not at levels and/or applied with modulation parameters suitable for preferential activation at the region of interest. However, once the region of interest is identified and targeted, the controller 18 may then operate in a treatment mode according to the modulation parameters associated with preferential activation or achieving other targeted physiological outcomes.

The controller 18 may also be configured to receive inputs related to the targeted physiological outcomes as an input to the selection of modulation parameters. For example, when an imaging modality is used to assess a tissue characteristic, the controller 18 may be configured to receive a calculated index or parameter of the characteristic. Based on whether the index or parameter is above or below a predefined threshold, a diagnosis may be made, and an indication of the diagnosis may be provided (e.g., via display 30). Additionally, or alternatively, the modulation parameters may be modified based on whether the index or parameter is above or below a predefined threshold. In one embodiment, the parameter can be a measure of tissue displacement of the affected tissue or a measure of depth of the effected tissue. Other parameters may include assessing a concentration of one or more molecules of interest (e.g., assessing one or more of a change in concentration relative to a threshold or a baseline/control, a rate of change, determining whether concentration is within a desired range, etc.).

In another implementation, a desired modulation parameter set may also be stored by the controller 18 (e.g., via memory 24). In this manner, subject-specific parameters may be determined. Further, the effectiveness of such parameters may be assessed over time. If a particular set of parameters is less effective over time, the subject may be developing insensitivity to activated pathways. If the system 10 includes an assessment device 20, the assessment device 20 may provide feedback to the controller 18. In certain embodiments, the feedback may be received from a user of an assessment device 20 indicative of a characteristic of the target physiological outcome. The controller 18 may be configured to cause the energy application device to apply energy according to modulation parameters and to dynamically adjust the modulation parameters based on the feedback. For example, based on the feedback, the processor 22 may automatically alter the modulation parameters (e.g., the frequency, amplitude, or pulse width of an ultrasound beam or mechanical vibration) in real time and responsive to feedback from the assessment device 20.

Further, the energy application device 12 (e.g., an ultrasound transducer) may operate under control of the controller 18 to: (a) acquire image data of a tissue that may be used to spatially select a region of interest within the target tissue, (b) apply the modulating energy to the region of interest, and (c) acquire an image to determine that the targeted physiological outcome associated with a change in a characteristic of interest has occurred (e.g., determine that a change in a glucose transporter pathway molecule and/or an incretin pathway molecule has occurred via a displacement measurement). In such an embodiment, the imaging device, the assessment device 20, and the energy application device 12 may be the same device.

The desired target tissue that includes the region of interest 16 (see FIG. 1) may be an internal tissue or an organ that includes synapses of axon terminals and non-neuronal cells. The synapses may be stimulated by direct application of energy to the axon terminals within a field of focus or focal zone of the energy application device 12 (e.g., ultrasound transducer) focused on the region of interest 16 of the target tissue to cause release of molecules into the synaptic space, e.g., the release of neurotransmitters and/or the change in ion channel activity in turn causes downstream effects. The region of interest 16 may be selected to include a certain type of axon terminal, such as an axon terminal of a particular neuron type and/or one that forms a synapse with a certain type of non-neuronal cell. Accordingly, the region of interest 16 may be selected to correspond to a portion of the target tissue with the desired axon terminals (and associated non-neuronal cells). The energy application may be selected to preferentially trigger a release of one or more molecules such as neurotransmitters from the nerve within the synapse or directly activate the non-neuronal cell itself through direct energy transduction (i.e., mechanotransduction or voltage-activated proteins within the non-neuronal cells), or cause an activation within both the neural and non-neuronal cells that elicits a desired physiological effect. The region of interest 16 may be selected as the site of nerve entry into the organ. In one embodiment, liver stimulation or modulation may refer to a modulation of the region of interest 16 at or adjacent to the porta hepatis. Acquisition of a treatment position may include selection of the region of interest 16, whereby the position on the patient's body at which the region of interest 16 is within the focal zone of the energy application device 12 when in operation is the treatment position.

The energy may be focused or substantially concentrated on a region of interest 16 and to only part of the internal tissue, e.g., less than about 50%, 25%, 10%, or 5% of the total volume of the tissue. That is, the region of interest 16 may be a sub-region of the internal tissue. In one embodiment, energy may be applied to two or more regions of interest 16 in the target tissue, and the total volume of the two or more regions of interest 16 may be less than about 90%, 50%, 25%, 10%, or 5% of the total volume of the tissue. In one embodiment, the energy is applied to only about 1%-50% of the total volume of the tissue, to only about 1%-25% of the total volume of the tissue, to only about 1%-10% of the total volume of the tissue, or to only about 1%-5% of the total volume of the tissue. In certain embodiments, only an axon terminal in the region of interest 16 of the target tissue would directly receive the applied energy and release neurotransmitters while the unstimulated axon terminals outside of the region of interest 16 do not receive substantial energy and, therefore, are not activated/stimulated in the same manner. In some embodiments, axon terminals in the portions of the tissue directly receiving the energy would induce an altered neurotransmitter release. In this manner, tissue subregions may be targeted for neuromodulation in a granular manner, e.g., one or more subregions may be selected. In some embodiments, the energy application parameters may be chosen to induce preferential activation of either neural or non-neuronal components within the tissue directly receiving energy to induce a desired combined physiological effect. In certain embodiments, the energy may be focused or concentrated within a volume of less than about 25 $mm^3$. In certain embodiments, the energy may be focused or concentrated within a volume of about 0.5 $mm^3$-50 $mm^3$. However, other focal volumes are also contemplated based on desired physiological outcomes. A focal volume and a focal depth for focusing or concentrating the energy within the region of interest 16 may be influenced by the size/configuration of the energy application device 12. The focal volume of the energy application may be defined by the field of focus or focal zone of the energy application device 12.

As provided herein, the energy may be substantially applied only to the region or regions of interest 16 to preferentially activate the synapse in a targeted manner to achieve targeted physiological outcomes. Accordingly, in certain embodiments, only a subset of a plurality of different types of axon terminals in the tissue is exposed to the direct energy application.

In certain embodiments, the target tissues that include the region of interest 16 are internal tissues or organs that include peripheral nerve endings or peripheral axon terminals. Contemplated tissue targets include gastrointestinal (GI) tissue (stomach, intestines), muscle tissue (cardiac, smooth and skeletal), epithelial tissue (epidermal, organ/GI lining), connective tissue, glandular tissues (exocrine/endocrine), etc. In one example, focused application of energy at a neuromuscular junction facilitates neurotransmitter release at the neuromuscular junction without an upstream action potential. In one embodiment, contemplated targets for modulation may include portions of a pancreas responsible for controlling insulin release or portions of the liver responsible for sensing glucose/metabolites and/or regulating their circulating concentrations.

While certain embodiments are disclosed in the context of ultrasound energy application, it should be understood that other energy types are contemplated, e.g., mechanical energy. Accordingly, the energy application device 12 may be configured as a mechanical vibrator to apply neuromodulating energy. Further, while certain embodiments of the disclosure are discussed in the context of ultrasound imaging data, the system 10 may be implemented to acquire alternative or additional types of imaging data to guide energy application to the region of interest 16.

As discussed above, the region of interest 16 may be at a significant depth beneath the surface of the subject's skin (e.g., in a range of 1-10 centimeters, 9-15 centimeters, 10-20 centimeters, etc.). Thus, effectively targeting and applying energy to the region of interest 16 may involve applying substantial pressure or force (e.g., in a range of 1-15 pounds-force) to press and hold the energy application device 12 inward against the subject's skin. Further, neuromodulation energy may be applied at a precise treatment site for an extended period of time (e.g., 30 minutes, 1 hour, etc.) in order to achieve a desired physiological outcome. Accordingly, human operators (e.g., clinicians, sonographers, etc.) may be unable to apply sufficient pressure and hold the energy application device 12 at the treatment site throughout the duration of treatment. Therefore, a positioner system 32 may be coupled to the energy application device 12 to apply sufficient pressure and hold the energy application device 12 at the precise treatment site associated with the region of interest 16.

Figure 3:
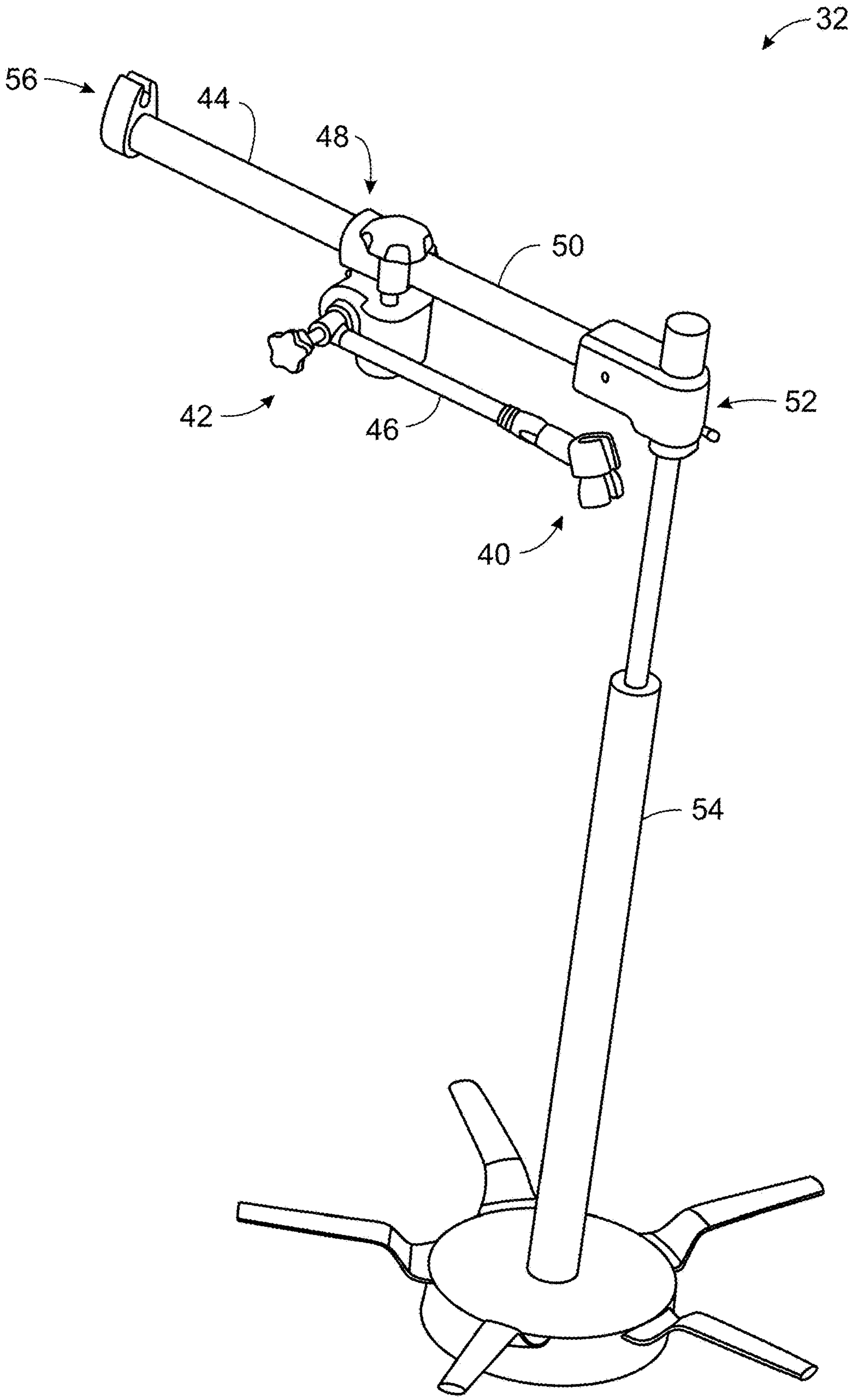
FIG. 3 is a perspective view of a positioner system for use with a neuromodulation system, such as the neuromodulation systems of FIGS. 1 and 2, according to embodiments of the present disclosure.

With the foregoing in mind, FIG. 3 is a perspective view of a positioner system 32 that may be used to facilitate neuromodulation. The positioner system 32 may include a probe holder 40, a pressure applicator 42, and a slider arm 44. As will be discussed in greater detail below, during operation, the probe holder 40 may receive and support an ultrasound probe or any other suitable energy application device 12. The pressure applicator 42 may be coupled to the probe holder 40 via a pivot arm 46. During operation, the pressure applicator 42 may rotate the pivot arm 46 in a direction towards the subject (e.g., patient) and apply steady pressure to maintain a position of the ultrasound probe within the probe holder 40 against the subject's skin. The pressure applicator 42 may also rotate the pivot arm 46 in a direction away from the subject to reduce or release the pressure against the subject. Accordingly, the pressure applicator 42 may adjustably apply pressure to the ultrasound probe while balancing patient comfort and application quality of the neuromodulation (e.g., accuracy of imaging and/or precision of energy application).

The pressure applicator 42 may be coupled to the slider arm 44 via a slide or slide mechanism 48 that may move along the slider arm 44 to adjust a position of the pressure applicator 42. The slider arm 44 may include a cantilever arm 50 with a mount 52 coupled to a support structure 54 on one end, and a stop or cord management feature 56 on the free end (e.g., end of the arm 50 opposite the mount 52). While FIG. 3 depicts the support structure 54 as a cart, the positioner system 32 may be coupled to any suitable support structure 54 (e.g., via the mount 52 of the slider arm 44). For example, in certain embodiments, the mount 52 may couple to a mobile stand, an operating table, a bed, a neuromodulation system cart or support, a fixture or support secured to surfaces or walls of a room, and the like. During operation, the slider arm 44 may be positioned to extend near or above the subject to suspend the pressure applicator 42 and probe holder 40 in a position to receive the ultrasound probe while the probe is at the treatment position on the subject's skin. As will be discussed in greater detail below, the probe holder 40 may be configured to allow for minor or fine (e.g., millimeter) adjustments of the position of the probe after it is coupled with the holder 40 and before pressure is applied via the pressure applicator 42. Accordingly, an operator may reposition the probe to more accurately target one or more areas of interest without having to decouple it from the positioner system 32.

In practice, the components of the positioner system 32 (e.g., probe holder 40, pressure applicator 42, and slider arm 44) are not expected to directly contact the subject's skin. Accordingly, the components of the positioner system may or may not be formed out of biocompatible materials (e.g., biosafe plastic polymers, ABS-M30). The positioner system 32 may be manufactured using any suitable materials capable of withstanding the mechanical and structural requirements of the system (e.g., able to withstand the pressures, forces, and cleaning processes associated with normal operation within a desired degree of safety).

The positioner system 32 may have multiple degrees of freedom or points of articulation to facilitate proper probe positioning and pressure application during neuromodulation across patients and treatments. That is, the positioner system 32 may be adjustable to ensure effective and repeatable results for a variety of patients with variations in anatomy (e.g., organ location, BMI, etc.), clinical conditions, and responsiveness to neuromodulation. The adjustability of the positioner system 32 may also facilitate repeatability (e.g., consistency of treatment) as a subject experiences changes over time associated with neuromodulation (e.g., weight loss associated with neuromodulation for metabolic disorders).

Figure 4:
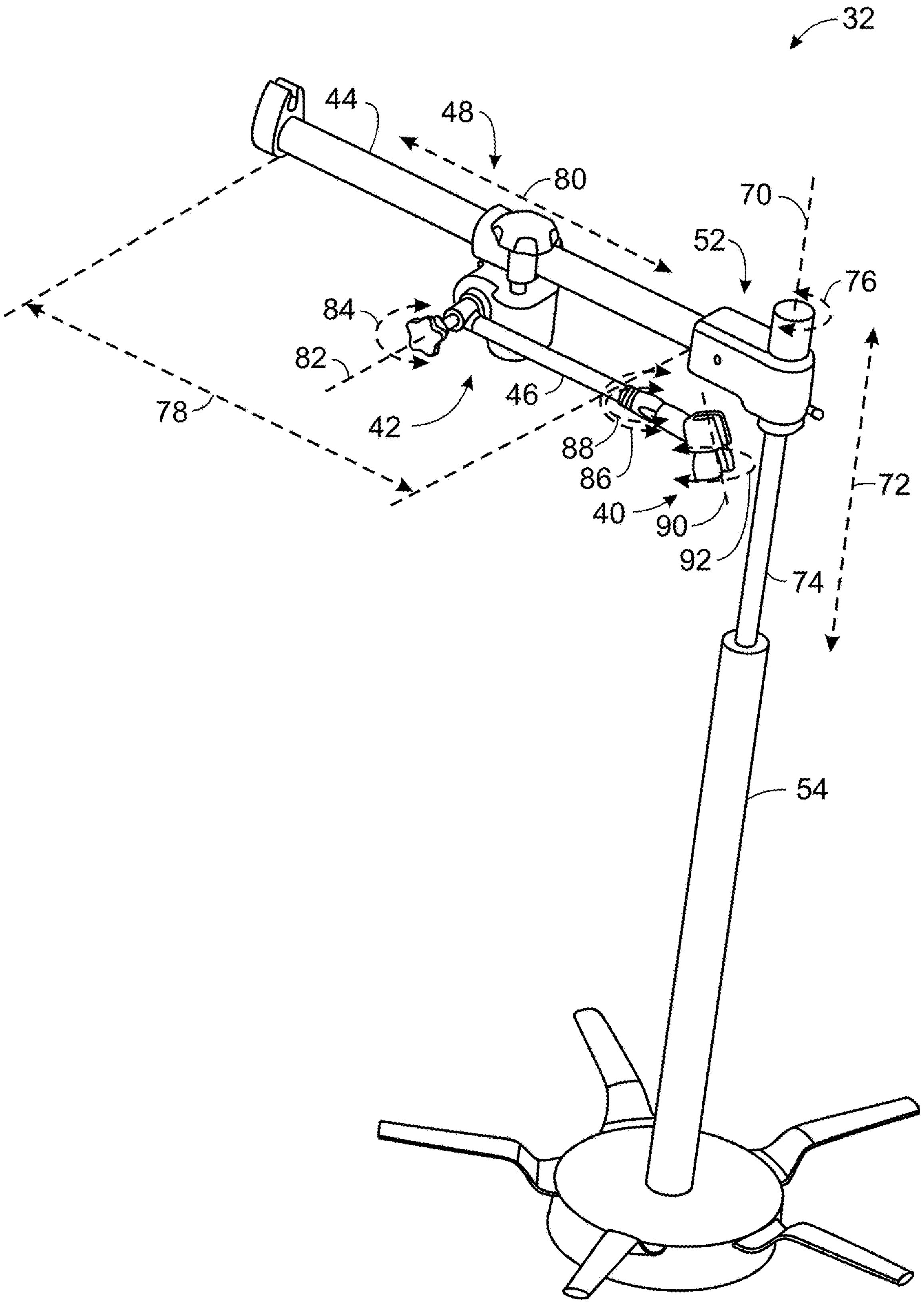
FIG. 4 illustrates exemplary points of articulation of the positioner system of FIG. 3, according to embodiments of the present disclosure.

FIG. 4 depicts exemplary degrees of freedom or points of articulation of the positioner system 32. As used herein, a point of articulation may be a point of connection between two bodies (e.g., components of the positioner system 32) which may allow relative motion between the two components in one or more directions (e.g., relative lateral motion) and/or about one or more axes (e.g., relative rotation). As used herein, degrees of freedom describe the number of independent ways a body (e.g., component of the positioner system 32) may move, such as translate along one or more axes and/or rotate about one or more axes. Thus, each point of articulation of the positioner system 32 may be associated with one or more degrees of freedom.

In some embodiments, the height of the positioner system 32 may be adjustable along an axis 70 corresponding to the support structure 54 and/or the mount 52 of the slider arm 44 (e.g., a vertical axis extending through the support structure 54 and/or mount 52), as indicated by arrows 72. For example, the support structure 54 (e.g., cart) may include a pneumatic arm 74 or any other suitable mechanism to adjust the height of the positioner system 32. Additionally, or alternatively, a height adjustment mechanism (e.g., pneumatic arm, actuator, etc.) may be integrated into the mount 52 of the slider arm 44. Further, the mount 52 may be rotatably coupled to the support structure 54, such that the slider arm 44 may rotate or pivot about the axis 70 as indicated by arrows 76 to allow for coarse swivel adjustments of the positioner system 32.

As mentioned above, the slider arm 44 may include a slide or slide mechanism 48 to adjust a position of the pressure applicator 42 along a length 78 of the slider arm 44, as indicated by arrows 80. The pivot arm 46 of the pressure applicator 42 may rotate about an axis 82 of the pressure applicator 42 (e.g., along a shaft coupling the pivot arm 46 to a gear assembly of the pressure applicator 42), as indicated by arrows 84. Accordingly, the pivot arm 46 may be rotated into or away from the subject, thereby allowing the pressure applicator 42 to adjustably apply pressure to an ultrasound probe during a neuromodulation treatment for patient comfort and quality of the neuromodulation (e.g., accuracy of imaging and/or precision of energy application). In some embodiments, the pivot arm 46 may include a ball joint on or proximate to an end of the pivot arm 46 coupled to the probe holder 40, thereby allowing the probe holder 40 to rotate relative to the pivot arm 46 in two planes, as indicated by arrows 86 and 88. Further, in certain embodiments, the probe holder 40 may removably couple to an ultrasound probe or other suitable energy application device 12 in such a manner as to allow for slight rotational adjustments of a position of the ultrasound probe about an axis 90 of the probe holder 40 (e.g., central axis), as indicated by arrows 92.

Therefore, as shown in FIG. 4, the positioner system 32 may have six points of articulation, each associated with one or more degrees of freedom, allowing for height adjustment (e.g., indicated by arrows 72), course swivel adjustments (e.g., of the slider arm 44 about the axis 70, as indicated by arrows 76), slide adjustments (e.g., of the slide mechanism 48 along the slider arm 44, as indicated by arrows 80), ball joint swivel adjustments (e.g., of probe holder 40 relative to pivot arm 46, as indicated by arrows 86 and 88), rotation adjustments (e.g., of probe about the axis 90, as indicated by arrows 92), and compression adjustments (e.g., of pivot arm 46 about the axis 82, indicated by arrows 82). Accordingly, the positioner system 32 may facilitate proper probe positioning and pressure application during neuromodulation across patients and treatments.

Figure 5:
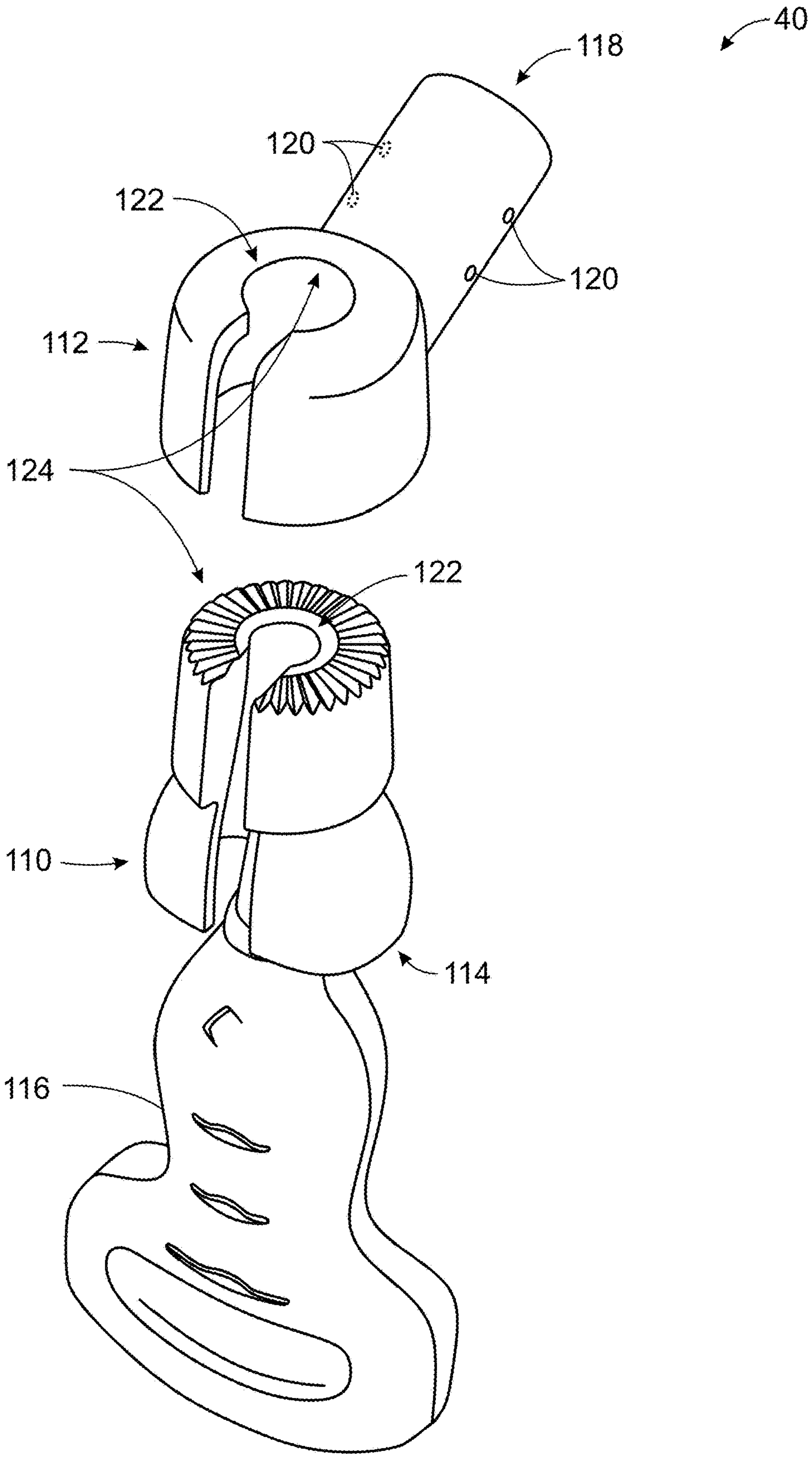
FIG. 5 is an exploded view of a probe holder of the positioner system of FIG. 3, according to embodiments of the present disclosure.

As discussed above, the probe holder 40 may removably couple to an ultrasound probe or other suitable energy application device 12 in such a manner as to allow for slight rotation of the probe relative to the probe holder 40. For example, FIG. 5 depicts an exploded view of an exemplary probe holder 40. In one embodiment, the probe holder 40 may include a lower receptacle 110 and an upper receptacle 112. The lower receptacle 110 may include one or more walls 114 formed to substantially match the profile (e.g., shape and curvature) of a portion of an ultrasound probe 116 (e.g., energy application device 12). That is, the walls 114 of the lower receptacle 110 may have dimensions substantially matching or corresponding to dimensions of the ultrasound probe 116 to define an interference or "snap" fit between the probe holder 40 and the ultrasound probe 116. Accordingly, the ultrasound probe 116 may be inserted into and/or removed from the probe holder 40 without using specialized tools or additional fasteners (e.g., screws, bolts, etc.) to couple and decouple the ultrasound probe 116 from the probe holder 40. Further, the ultrasound probe 116 may substantially retain its profile when inserted into the probe holder 40 due to the shape and curvature of the walls 114 of the lower receptacle 110. Thus, the ultrasound probe 116 may have substantially the same hand feeling when coupled or uncoupled from the positioner system 32. Accordingly, an operator may intuitively adjust the position of the ultrasound probe 116 while it is coupled to the positioner system using muscle memory of "free scanning" with the ultrasound probe 116 uncoupled from positioner system 32. Additionally, properly inserting the ultrasound probe 116 into the probe holder 40 (e.g., lower receptacle 110) may cause an audible sound (e.g., snap) indicating proper coupling.

The upper receptacle 112 may be rotatably coupled to the pivot arm 46. For example, a shaft with a non-circular or flat area (e.g., rectangular cross section) extending from the ball joint in the pivot arm 46 may be inserted into an end 118 of the upper receptacle 112 and fastened into place using set screws, or any suitable fastener, inserted into the side of the upper receptacle 112 (e.g., via one or more apertures or holes 120 on opposite sides of the upper receptacle 112). Therefore, the probe holder 40 may rotate relative to the pivot arm 46 of the pressure applicator 42 as discussed above.

The lower receptacle 110 and the upper receptacle 112 may each include an opening 122 to allow a cord of the ultrasound probe 116 to extend out and through the probe holder 40. In some embodiments, mating ends 124 of the lower receptacle 110 and the upper receptacle 112 (e.g., an internal surface of the upper receptacle 112 and an external surface of the lower receptacle 110) may include corresponding coupling elements, such as interfacing teeth, to allow relative motion (e.g., rotation) between the lower receptacle 110 and the upper receptacle 112 when pressure is not being applied via the pressure applicator 42, and to prevent relative motion when pressure is applied. For example, as shown in FIG. 6, the lower receptacle 110 may rotate (e.g., clockwise, counterclockwise) relative to the upper receptacle 112 about a central axis of the probe holder (e.g., axis 90), as indicated by arrows 92, until pressure is applied via the pressure applicator 42, as shown by arrow 130.

As mentioned above, the mating ends 124 of the lower receptacle 110 and the upper receptacle 112 may include interfacing teeth to facilitate coupling between components of the probe holder 40. Referring closely to FIG. 7, before pressure is applied via the pressure applicator 42, a gap 140 may be formed between the complementary teeth 142 of the lower receptacle 110 and the teeth 144 of the upper receptacle 112. Accordingly, the lower receptacle 110 may "float" within the upper receptacle 112. That is, the lower receptacle 110 may incrementally rotate relative to the upper receptacle 112 (as shown in FIG. 6) due to the gap 140 between the interfacing teeth 142, 144. An inner surface of the upper receptacle 112 may include a ridge or a groove 145 to interface with the lower receptacle 110 and allow the lower receptacle to "float" within the upper receptacle 112 without decoupling from the upper receptacle 112. Thus, an operator (e.g., sonographer) may fine tune the position of the ultrasound probe 116 after the probe 116 is inserted into the probe holder 40 (e.g., make millimeter adjustments of the position). When pressure is applied via the pressure applicator 42, the upper receptacle 112 will be driven towards the lower receptacle 110, thereby closing the gap 140, and causing the teeth 142 of the lower receptacle 110 and the teeth 144 of the upper receptacle 112 to interlock. Accordingly, the position of the ultrasound probe 116 relative to the probe holder 40 will be locked (e.g., held constant) via the pressure application, without any additional action from the operator.

Figure 6:
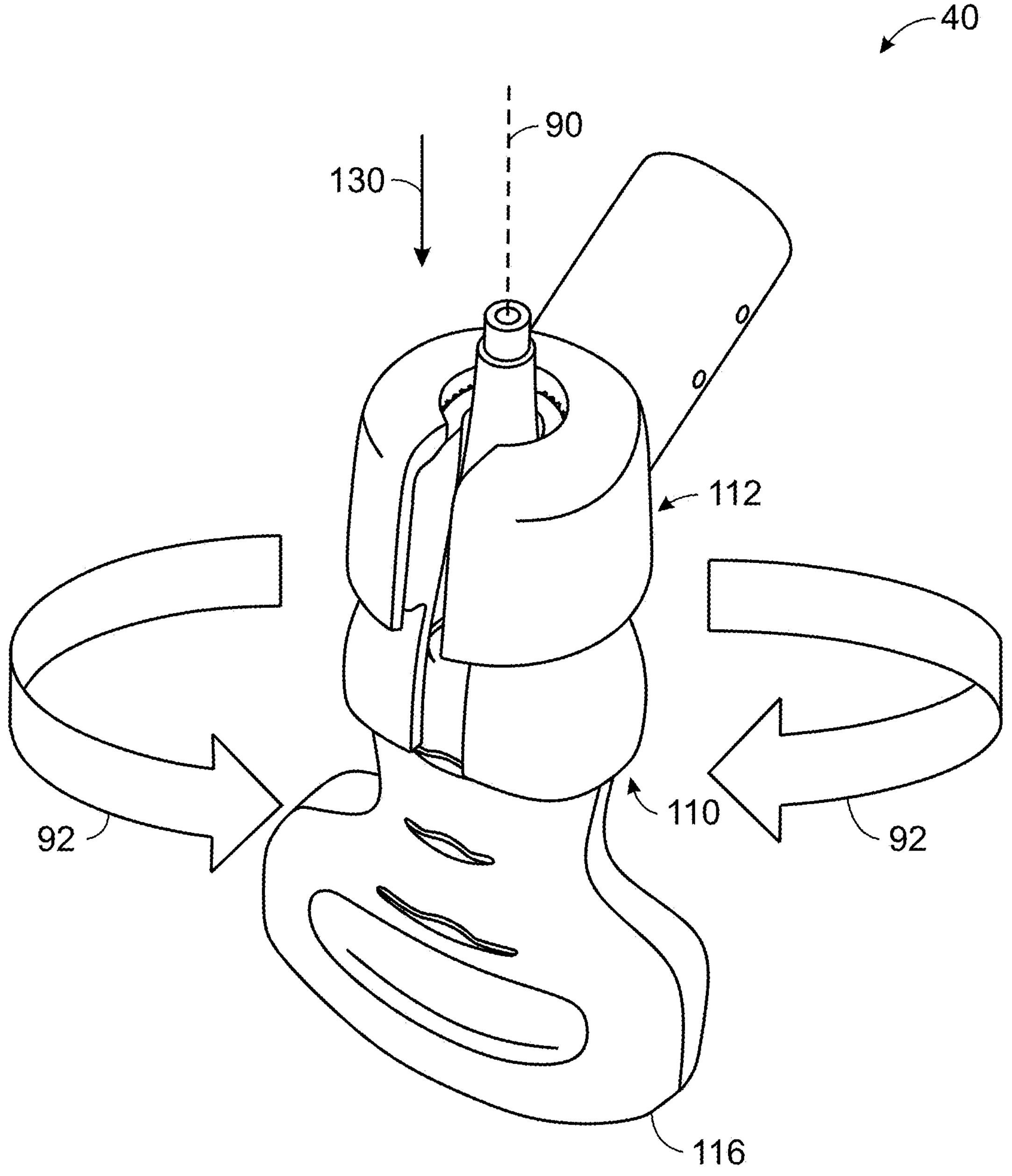
FIG. 6 is a perspective view of the probe holder of FIG. 5, according to embodiments of the present disclosure.
Figure 7:
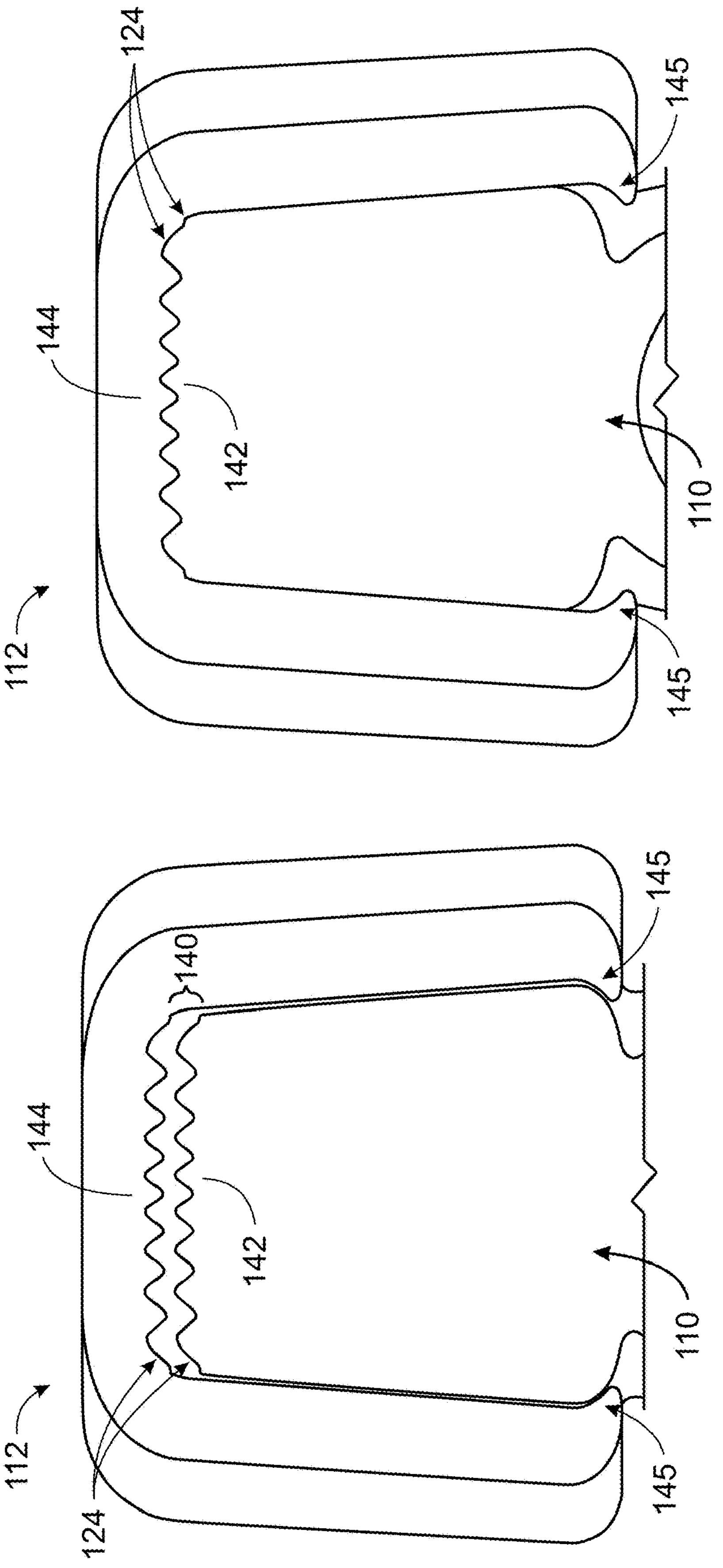
FIG. 7 illustrates detailed views of exemplary mating ends of a lower receptacle and an upper receptacle of the probe holder of FIG. 5, according to embodiments of the present disclosure.

While FIGS. 5-7 depict the probe holder 40 as a two-piece assembly with a lower receptacle 110 and an upper receptacle 112, the probe holder 40 may include a single receptacle. For example, in certain embodiments, an upper portion of an ultrasound probe 116 may include features substantially the same as those of the lower receptacle 110 (e.g., an upper surface with interfacing teeth). That is, the lower receptacle 110 may be integrated into the ultrasound probe 116. Accordingly, the probe holder 40 may include a single receptacle substantially similar to the upper receptacle 112, to rotatably couple to the pivot arm 46 of the pressure applicator 42 and to removably couple to the ultrasound probe 116. In such embodiments, mating ends of the ultrasound probe 116 and the single receptacle may include interfacing teeth to allow or prevent relative motion between the probe 116 and the probe holder depending on whether or not pressure is being applied by the pressure applicator 42, as described above with regards to FIG. 7.

Figure 8:
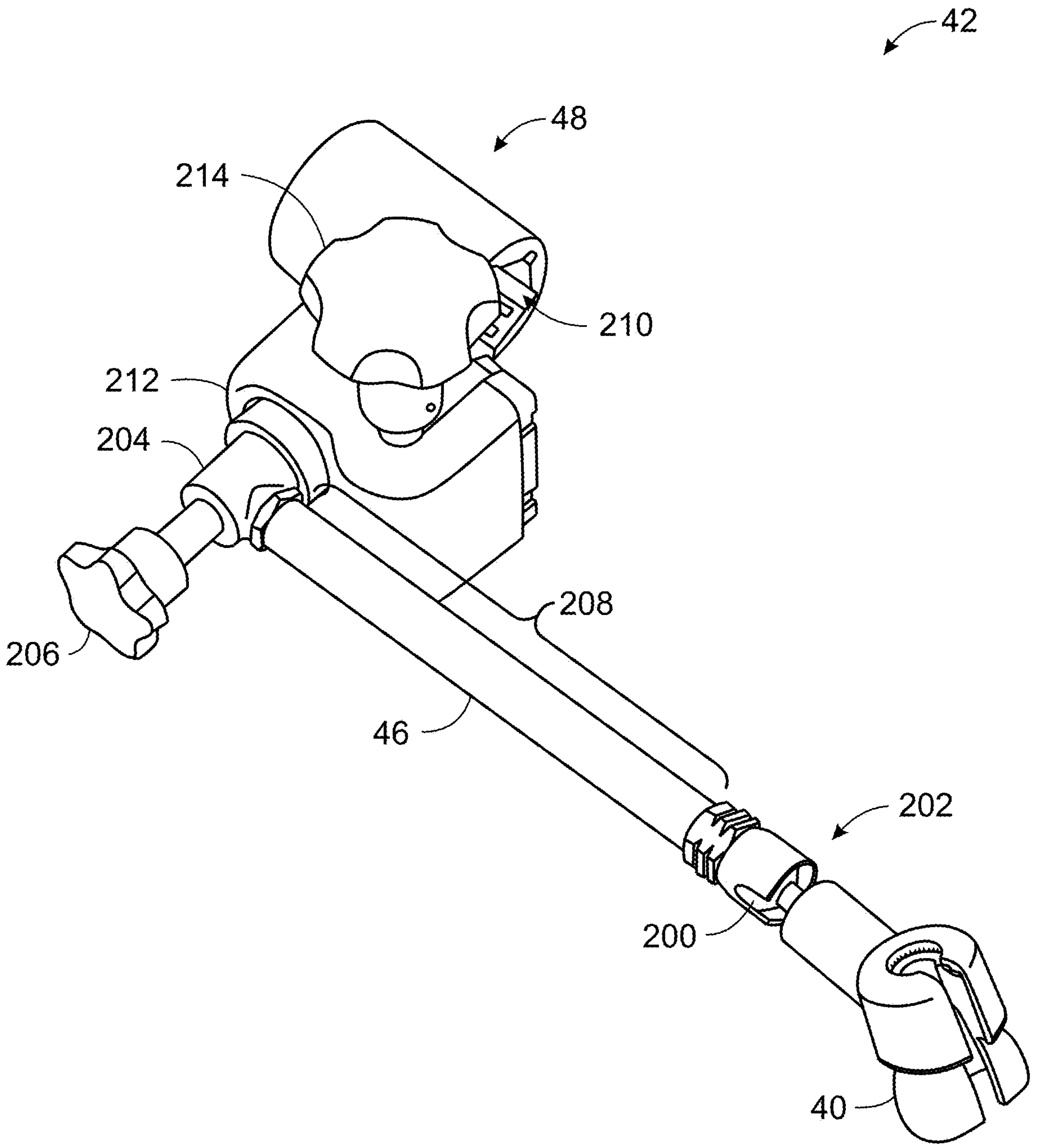
FIG. 8 is a perspective view of a pressure applicator of the positioner system of FIG. 3, according to embodiments of the present disclosure.

FIG. 8 shows a perspective view of the pressure applicator 42 coupled to the probe holder 40 and to the slide 48 of the positioner system 32. As discussed above, the pressure applicator 42 may include a pivot arm 46 coupled to the probe holder 40. For example, the pivot arm 46 may include a ball joint 200 on or proximate to an end 202 of the pivot arm 46 to rotatably couple to the probe holder 40. That is, the ball joint 200 may allow the probe holder 40 to rotate relative to the pivot arm 46. The pivot arm 46 may include an internal mechanism to lock and unlock the ball joint 200 (e.g., prevent or allow movement/rotation). The internal mechanism may include a wedge mechanism at or proximate to a second end 204 of the pivot arm 46 (e.g., opposite of end 202) controlled via rotation of a positioner lock knob (e.g., first knob) 206 of the pressure applicator 42. The internal mechanism may also include a push rod extending along a length 208 of the pivot arm 46 with a cup formed on an end of the push rod (e.g., proximate to the end 202 of the pivot arm 46). When the positioner lock knob 206 is rotated in a first direction (e.g., clockwise), the wedge mechanism may drive against the push rod, thereby causing the push rod to extend (e.g., move along the length 208 of the pivot arm 46 toward the end 202) such that the cup interfaces with and binds the ball joint 200 (e.g., prevents movement/rotation of the ball joint 200). When the positioner lock knob 206 is rotated in a second direction (e.g., counterclockwise), the wedge mechanism may stop interfacing with (e.g., driving) the push rod, thereby causing the push rod to return to its neutral position (e.g., retract along the length 208 of the pivot arm 46 toward the end 204) such that the cup disengages with the ball joint 200 and allows the ball joint 200 to rotate.

Rotating the positioner lock knob 206 in the first direction may also prevent motion of the slide 48 along the slider arm 44. The slide 48 may be a sliding collar with an internal surface or profile 210 corresponding to the slider arm 44. That is, the internal surface 210 may substantially match the shape and size of a cross section of the slider arm 44 to allow the slide 48 to move along the slider arm 44. For example, the internal surface 210 may be hexagonal to allow motion along a hexagonal slider arm 44. As will be discussed in greater detail with regards to FIG. 10, the slide 48 may be substantially similar to a C-clamp or C-clip, with a gap formed between the sides of the slide 48 to allow the slide 48 to move along the slider arm 44. A shaft of the positioner lock knob 206 may extend between the sides of the slide 48, with motion constrained between the shaft and a side of the slide (e.g., one end of the shaft may include features substantially similar to a bolt, such as a hexagonal face constrained in a hexagonal cut out in the side of the slide). A portion of the shaft may be threaded complimentary with the positioner lock knob 206. Accordingly, when the positioner lock knob 206 is rotated in a first direction (e.g., clockwise), the positioner lock knob 206 may translate along the shaft in a first direction (e.g., in a direction towards the pressure applicator 42) and draw the sides of the slide 48 together, closing the gap between the sides of the slide 48 and preventing movement of the slide 48. When the positioner lock knob 206 is rotated in the second direction (e.g., counterclockwise), the positioner lock knob 206 may translate along the shaft in a second direction (e.g., in a direction away from the pressure applicator 42) and push the sides of the slide 48 apart, forming the gap between the sides of the slide 48 and allowing movement of the slide 48.

Therefore, the positioner lock knob 206 may be used to prevent relative motion between the probe holder 40 and the pivot arm 46 and relative motion of the pressure applicator 42 along the slider arm 44 via the slide 48. As discussed above, the probe holder 40 may allow for fine (e.g., millimeter) adjustments of the position of the ultrasound probe 116 until pressure is applied via the pressure applicator 42. The pressure applicator 42 may include a worm gear system 212, controlled via the positioner lock knob (e.g., first knob) 206 and a compression adjustment knob (e.g., second knob) 214, to adjustably apply pressure. The worm gear system 212 may allow for gradual and steady pressure application, thereby preventing or reducing large and sudden changes in applied pressure which may lead to patient discomfort. Additionally, the worm gear system may prevent backlash between components of the positioner system 32.

Figure 9:
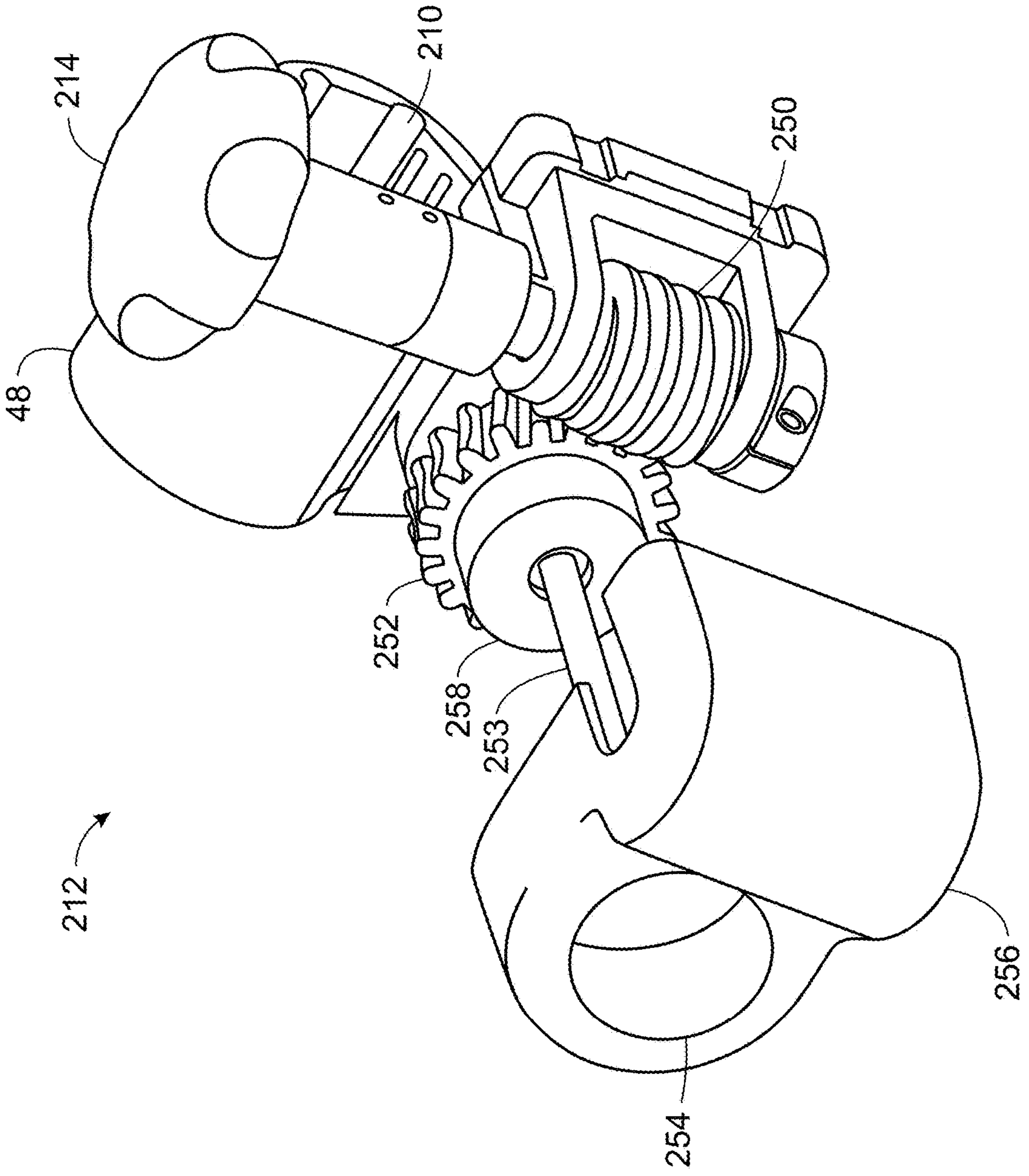
FIG. 9 is an exploded view of a worm gear system of the pressure applicator of FIG. 8, according to embodiments of the present disclosure.

Referring closely to FIG. 9, the compression adjustment knob 214 may be coupled to a worm gear 250 of the worm gear system 212. Accordingly, when the compression adjustment knob 214 is rotated, the worm gear 250 rotates and causes a ring gear 252 of the worm gear system 212 to rotate. While not shown, the positioner lock knob 206 may interface with the ring gear 252. For example, the shaft 253 of the positioner lock knob 206 may extend through the pivot arm 46 (e.g., at or proximate to the end 204) and through an aperture 254 (e.g., opening) in a housing 256 of the worm gear system 212, and couple to a rubberized washer within the housing 256. As discussed above, when the positioner lock knob 206 is rotated in a first direction (e.g., clockwise), the internal mechanism of the pivot arm 46 may bind the ball joint 200 and prevent relative motion between the probe holder 40 and the pivot arm 46, and the positioner lock knob 206 may translate along the shaft 253 in a direction towards the worm gear system 212 and close the gap between the sides of the slide 48 to prevent relative motion of the pressure applicator 42 along the slider arm 44. The internal mechanisms of the pressure applicator 42 may be configured such that rotating the positioner lock knob 206 in the first direction locks each degree of freedom simultaneously, such that relative motion between the probe holder 40 and the pivot arm 46 is prevented at the same time as relative motion of the pressure applicator 42 along the slider arm 44. Accordingly, the positioner lock knob 206 may sinch the components of the positioner system 32 together (e.g., prevent relative motion between the components). Further, rotating the positioner lock knob 206 in the first direction may cause the rubberized washer to contact a face 258 of the ring gear 252, thereby preventing relative motion between the components of the positioner system and the ring gear 252. Accordingly, when the ring gear 252 is rotated via rotation of the worm gear 250, the pivot arm 46 rotates.

Therefore, rotating the compression adjustment knob 214 in a first direction (e.g., clockwise) may rotate the pivot arm 46 into the subject with a steady and gradual pressure. Rotating the compression adjustment knob 214 in a second direction (e.g., counterclockwise) may rotate the pivot arm 46 away from the subject. Thus, if the subject experiences discomfort, the operator may rotate the compression adjustment knob 214 in the second direction to reduce the pressure applied without changing the position of the ultrasound probe 116. Additionally, if the treatment requires greater pressure (e.g., for effective application of neuromodulation energy and/or effective imaging), the operator may rotate the compression adjustment knob 214 in the first direction to increase the pressure applied without changing the position of the ultrasound probe 116. When the treatment is over, the operator may rotate the positioner lock knob 206 in the second direction to release the pressure applied and allow relative motion between components of the positioner system 32. Accordingly, the pressure applicator 42 may be used to maintain a constant position of the ultrasound probe 116 against the subject (e.g., at a treatment position associated with a region of interest) and adjustably apply pressure to the ultrasound probe 116 to balance patient comfort and application quality throughout the duration of treatment.

Figure 10:
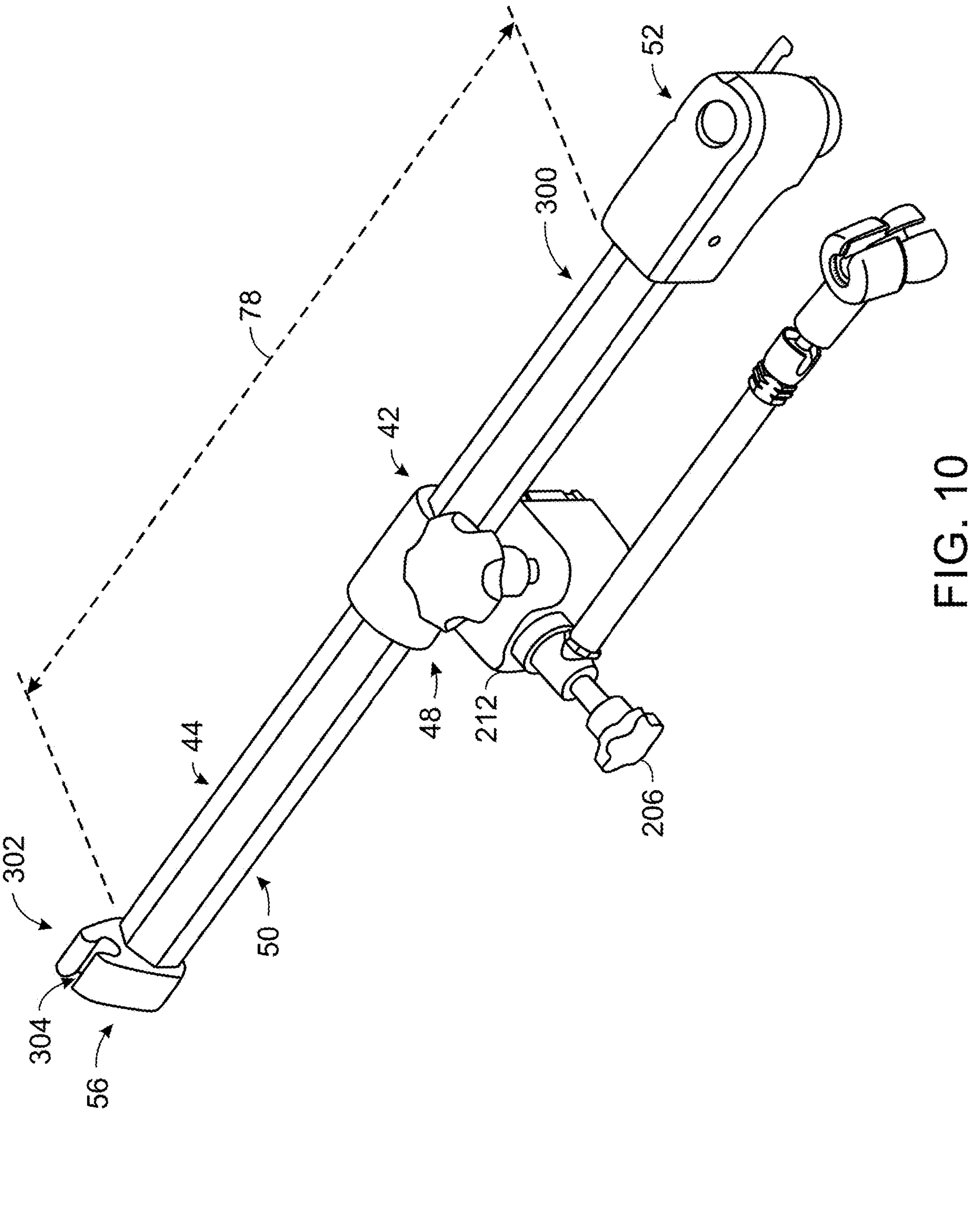
FIG. 10 is a perspective view of a slider arm of the positioner system of FIG. 3, according to embodiments of the present disclosure.
Figure 11:
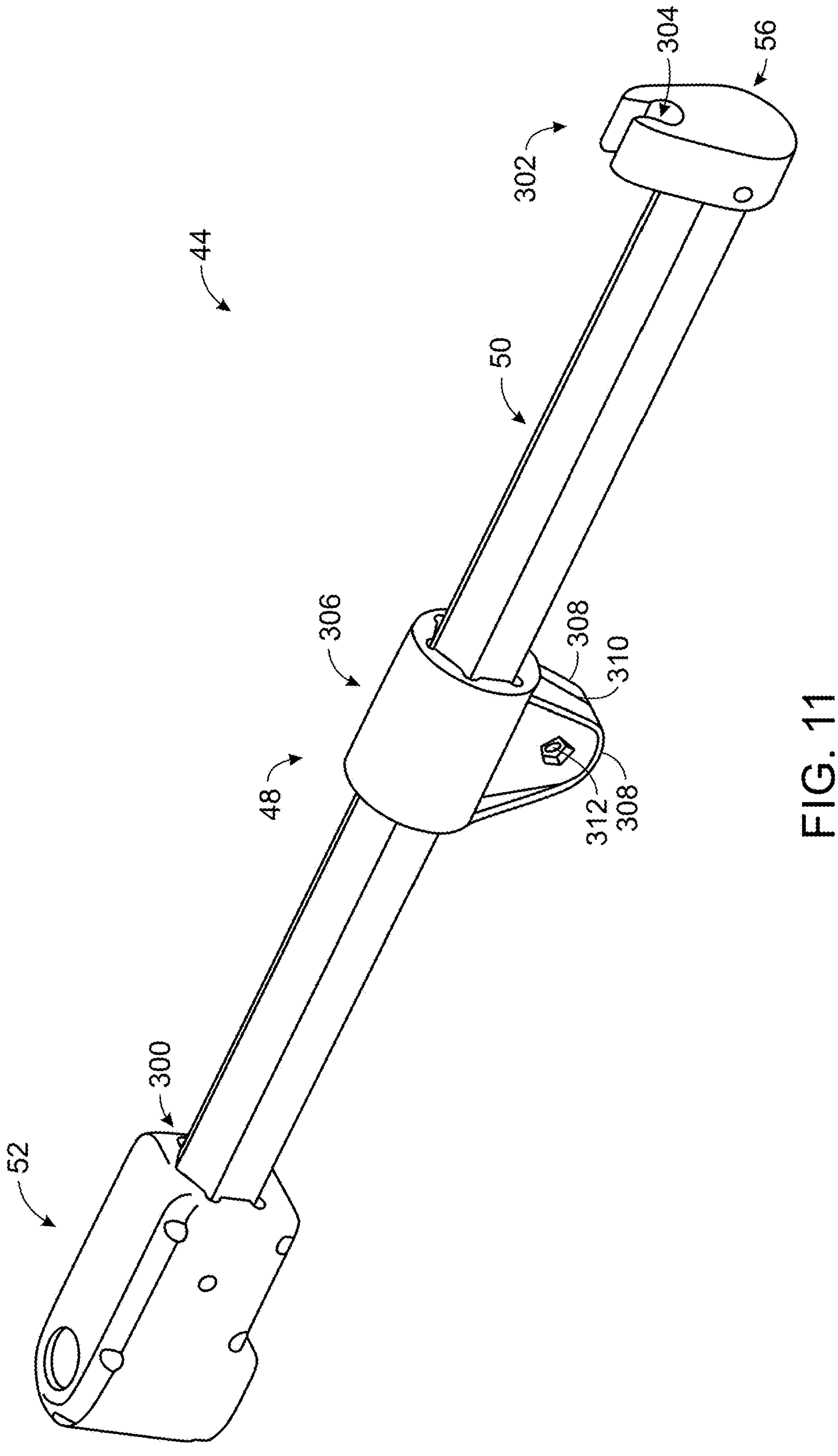
FIG. 11 is a perspective view of the slider arm of FIG. 10 without the pressure applicator of FIG. 8 installed, according to embodiments of the present disclosure.

The pressure applicator 42 and probe holder 40 may be suspended above or near the subject and supported by the slider arm 44 of the positioner system 32. FIGS. 10 and 11 show perspective views of an embodiment of the slider arm 44. As discussed above, the slider arm 44 may include a cantilever arm 50 with a mount 52 coupled to one end 300 and a stop or cord management feature 56 coupled to a second end 302 (e.g., opposite of end 300). The mount 52 may couple to any suitable support structure (e.g., support structure 54) capable of supporting the weight of the positioner system 32 and the withstanding/supporting the pressure applied by the positioner system 32. For example, the mount 52 may couple to a weighted cart, a mobile stand, an operating table, a bed, a neuromodulation system controller (e.g., controller 18), a wearable device, and the like.

The cord management feature may include a groove (e.g., indentation, opening, etc.) 304 configured to accommodate and receive a cord of the ultrasound probe 116 (e.g., a cord configured to transport ultrasound signals, control signals, power signals, or a combination thereof). Accordingly, the dimensions and shape (e.g., depth, diameter, curvature, etc.) of the groove 304 may substantially match the dimensions and shape (e.g., depth, diameter, curvature, etc.) of the cord. During operation, the cord may extend through one or more openings 122 in the receptacle(s) of the probe holder 40 and may be inserted into the cord management feature 56. Accordingly, the cord management feature 56 may reduce the cable weight on the ultrasound probe 116 and prevent the cord from hanging or resting on the subject or operator, thereby improving application quality and comfortability. The cord management feature 56 may also prevent the slide 48 from sliding off the free end (e.g., end 302) of the slider arm 44.

In some embodiments, the slider arm 44 may have one or more features to limit or prevent free radial rotation of the slider arm 44. For example, as shown in FIGS. 10 and 11, the cantilever arm 50 of the slider arm 44 may have a hexagonal cross section to prevent radial rotation of the pressure applicator 42 about the slider arm 44. As discussed above, the slide 48 coupling the pressure applicator 42 to the slider arm 44 may have an internal surface or profile 210 substantially matching the cross section. Accordingly, during operation, the pressure applicator 42 may be repositioned at different angles on the arm 50 by removing the cord management feature 56 from the end 302 of the arm 50, removing the slide 48 (e.g., sliding the slide 48 off the end 302), rotating the slide to the desired angle, and reinstalling the slide 48 (e.g., sliding the slide 48 onto the end 302 and recoupling the cord management feature 56 to the end 302). Therefore, the angle (e.g., angular position) of the pressure applicator 42 may be adjusted according to a number of fixed angles defined by the slider arm 44 (e.g., by respective sides of the arm 50) to accommodate various patient positions, while remaining fixed throughout the duration of treatment. While FIGS. 10 and 11 show the slider arm 44 with a hexagonal cross section, the slider arm 44 may have any suitable cross section (e.g., octagonal, square, triangular, circular, etc.). In embodiments where the slider arm 44 includes a circular or rounded cross section, the slider arm 44 may include alternative features to limit or prevent free radial rotation of the pressure applicator 42 about the slider arm 44 and/or free radial rotation of the slider arm about the mount 52. For example, in certain embodiments, the slider arm 44 may include a slot or flat spot on a surface of the arm 50 in order to prevent free rotation, while allowing for fixed, discrete angular adjustments.

As discussed above, the slide 48 may move along the length 78 of the slider arm 44 to adjust the position of the pressure applicator 42. Referring closely to FIG. 11, the slide 48 may include a collar feature 306 configured to couple to and slide along the slider arm 44 (e.g., with the inner surface 210 substantially matching the cross section of the slider arm 44) and two sides 308 extending from the collar feature 306 and forming a gap 310 to allow the slide 48 to move along the slider arm 44. (i.e., the collar feature 306 may not extend around the entire circumference or outer surface of the slider arm 44). As discussed above, a portion of the shaft 253 of the positioner lock knob 206 may interface with a cut out or opening 312 in one of the sides 308 when the pressure applicator 42 is installed on the slider arm 44. For example, one end of the shaft 253 may include features substantially similar to a bolt, such as a hexagonal face, which may interface with the cut out 312, which may have a corresponding shape and size to the face of the shaft, to prevent motion between the shaft 253 and the slide 48. When the positioner lock knob 206 is rotated in the first direction (e.g., clockwise), the positioner lock knob 206 may translate along the shaft 253 in a direction towards the pressure applicator 42 and draw the sides 308 together, thereby closing the gap 310 and preventing movement of the slide 48 along the slider arm 44. When the positioner lock knob 206 is rotated in the second direction (e.g., counterclockwise), the positioner lock knob 206 may translate along the shaft 253 in a direction away from the pressure applicator 42 and push the sides 308 apart, thereby reforming the gap 310 and allowing movement of the slide 48 along the slider arm 44. Accordingly, the positioner lock knob 206 of the pressure applicator 42 may be used to prevent and allow motion of the slide 48 along the slider arm 44.

Figure 12:
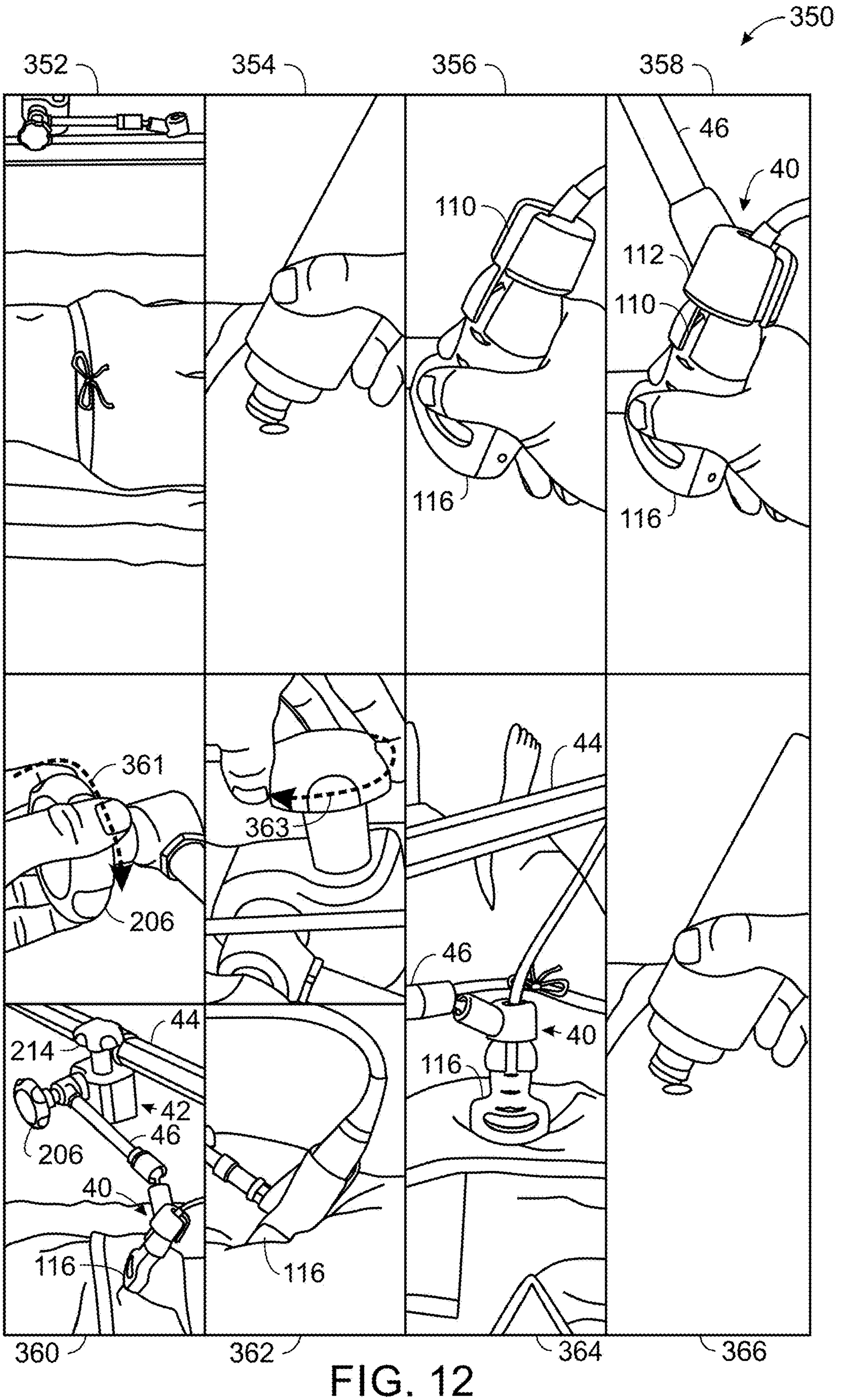
FIG. 12 is an exemplary workflow of a method for administering a therapy dose of ultrasound energy using a neuromodulation system including the positioner system of FIG. 3, according to embodiments of the present disclosure.

With the foregoing in mind, FIG. 12 depicts an exemplary workflow of a method 350 for administering a therapy dose of ultrasound energy using a neuromodulation system including the positioner system 32 according to embodiments of the present disclosure. The method 350 includes various steps represented by images. Although the exemplary workflow illustrates the steps in a certain sequence, it should be understood that the steps may be performed in any suitable order and certain steps may be carried out simultaneously, where appropriate. Additionally, steps may be added or omitted from the method 350.

The method 350 may begin at step 352, in which an operator (e.g., clinician, sonographer) may position the subject (e.g., patient) in preparation for application of ultrasound energy to cause neuromodulation in the subject. The operator may position the subject based on a region of interest (e.g., region of interest 16). As previously described in regards to FIGS. 1 and 2, the region of interest 16 may correspond to one or more internal tissues or organs that include peripheral nerve endings or peripheral axon terminals, such as portions of the liver, pancreas, gastrointestinal (GI) tissue (stomach, intestines), and the like. Accordingly, the operator may position the subject on their back, side, or any suitable position to target the region of interest 16. The operator may take a few minutes (e.g., 1-2 minutes, 1-5 minutes) to position the patient.

At step 354, the operator may apply ultrasound gel or an ultrasound gel pad to the subject's skin in preparation for application of ultrasound energy. The operator may apply the ultrasound gel or ultrasound gel pad to a portion of the subject's skin based on the area of interest, such as a portion of the subject's skin below the ribcage, in between two ribs, and the like. The ultrasound gel or ultrasound gel pad may improve the imagining quality and energy application by coupling the ultrasound probe 116 to the subject's skin and removing or reducing air pockets between the ultrasound probe 116 and the patient's skin, thereby improving the transmission of energy into the subject's skin towards the region of interest 16. The operator may take a few seconds (e.g., 1-10 seconds, 1-30 seconds) to apply the ultrasound gel or ultrasound gel pad.

At step 356, the operator may "free scan" with the ultrasound probe 116 to determine a treatment position of the ultrasound probe 116 associated with the region of interest 16 for neuromodulation. That is, the operator may use the ultrasound probe 116 while it is disconnected from the positioner system 32 to acquire image data of the subject in order to identify the region of interest 16 and determine the treatment position on the subject's skin based on the region of interest 16. In certain embodiments, the operator may free scan with the ultrasound probe 116 with the lower receptacle 110 of the probe holder 40 coupled to the ultrasound probe 116 while the lower receptacle 110 is decoupled from the upper receptacle 112, and thus, the rest of the positioner system 32. The operator may take a few minutes (e.g., 1-2 minutes, 1-5 minutes) to acquire the image data and determine a treatment position by free scanning with the ultrasound probe 116.

At step 358, the operator may position the ultrasound probe 116 on or over the treatment position and may couple the ultrasound probe 116 to the positioner system 32. For example, once the treatment position is identified, the operator may hold the ultrasound probe 116 on or over the treatment position and may bring the probe holder 40 of the positioner system 32 to the ultrasound probe 116. The operator may rotate the slider arm 44 to extend above or near the subject, adjust a position of the pressure applicator 42 along the slider arm 44 via the slide 48, rotate the probe holder 40 relative to the pivot arm 46 (e.g., via ball joint 200), and the like, or any combination thereof, to bring the probe holder 40 to the ultrasound probe 116. The operator may then insert or affix the ultrasound probe 116 to the probe holder 40 (e.g., by inserting the ultrasound probe into the lower and/or upper receptacle 110, 112 of the probe holder 40). The operator may make adjustments to the position of the ultrasound probe 116 after the ultrasound probe 116 is coupled with the probe holder 40 (e.g., by rotating the probe 116 relative to the pivot arm 46), as needed. The operator may take a few seconds (e.g., 1-5 seconds, 1-10 seconds, 1-30 seconds, 1-60 seconds) to position the ultrasound probe 116 and couple the ultrasound probe 116 to the probe holder 40 of the positioner system 32.

Once the ultrasound probe 116 is in the treatment position and coupled to the positioner system 32, at step 360, the operator may lock the position of the ultrasound probe 116 via the positioner system 32. That is, the operator may rotate the positioner lock knob 206 in a first direction (e.g., clockwise), as indicated by arrow 261, to prevent relative motion between components of the positioner system 32. As discussed above, rotating the positioner lock knob 206 in the first direction may cause the internal mechanism of the pivot arm 46 to bind the ball joint 200, thereby preventing relative motion between the probe holder 40 and the pivot arm 46 of the pressure applicator 42. Additionally, rotating the positioner lock knob 206 in the first direction may cause the positioner lock knob 206 to translate along its shaft 253 towards the pressure applicator 42 and close the gap 310, thereby preventing relative motion of the pressure applicator 42 along the slider arm 44 by locking the slide 48 in place. The internal mechanisms of the pressure applicator 42 may be configured such that rotating the positioner lock knob 206 in the first direction locks each degree of freedom simultaneously, such that relative motion between the probe holder 40 and the pivot arm 46 is prevented at the same time as relative motion of the pressure applicator 42 along the slider arm 44. The probe holder 40 may include features (e.g., interfacing teeth on mating ends of the lower receptacle 110 and the upper receptacle 112 or interfacing teeth on the mating ends of the ultrasound probe 116 and the receptacle) to allow the operator to make additional fine (e.g., millimeter) adjustments to the position of the ultrasound probe 116 after positioner lock knob is rotated in the first direction (e.g., by rotating the probe 116 relative to the pivot arm 46), as needed. The operator may take a few seconds (e.g., 1-5 seconds, 1-10 seconds, 15-30 seconds) to prevent relative motion between components of the positioner system 32 via the positioner lock knob 206 of the positioner system 32.

At step 362, the operator may apply pressure to the ultrasound probe 116 via the positioner system 32. For example, the operator may rotate the compression adjustment knob 214 in a first direction (e.g., clockwise), as indicated by arrow 363, to rotate the pivot arm 46 into the subject, thereby pressing the ultrasound probe 116 against the treatment position with a steady pressure. The pressure applicator 42 may be configured to apply a substantial amount of pressure or force (e.g., in a range of 1-15 pounds-force) to drive the ultrasound probe 116 into the subject's skin via the pivot arm 46, as the region of interest may be at a significant depth beneath the surface of the subject's skin (e.g., in a range of 1-10 centimeter, 9-15 centimeters, 10-20 centimeters, etc.). The operator may rotate the compression adjustment knob 214 in a second direction (e.g., counterclockwise, opposite the first direction) to reduce the amount of pressure applied to the ultrasound probe and may rotate the compression adjustment knob in the first direction to increase the amount of pressure applied. As discussed above, the interfacing teeth of the probe holder (e.g., on mating ends of the lower receptacle 110 and the upper receptacle 112, on mating ends of the ultrasound probe 116 and the receptacle) may interlock when pressure is applied to the ultrasound probe 116. Accordingly, the positioner system 32 may lock the ultrasound probe 116 into position against the subject's skin with a desired amount of pressure. The operator may take a few seconds (e.g., 1-5 seconds, 1-10 seconds, 15-30 seconds) to adjustably apply pressure to the ultrasound probe 116 via the positioner lock knob 206 of the positioner system 32.

At step 364, the operator may apply a therapy dose of ultrasound energy through the subject's skin to the region of interest (e.g., conduct treatment). For example, the operator may use the ultrasound probe 116 to direct energy pulses towards the region of interest of an internal tissue or organ of the subject (e.g., a peripheral tissue) to achieve a targeted physiological outcome, as described in FIGS. 1 and 2. The treatment duration may last for various time periods, including but not limited to, from a few minutes to several hours, in order to achieve the targeted physiological outcome. That is, the operator may apply ultrasound energy to the region of interest for 15 minutes, 30 minutes, an hour, and the like. After the treatment is administered via the ultrasound probe 116 to the region of interest, the operator may rotate the positioner lock knob 206 in a second direction (e.g., counterclockwise) to release the pressure and allow motion between components of the positioner system 32.

At step 366, the operator may repeat steps 352-364 as many number of times as desired (e.g., in order to target each of the one or more regions of interest, in order to achieve/follow a treatment protocol of multiple therapy doses, etc.), before cleaning and disinfecting the ultrasound probe 116 and the subject's skin (e.g., to limit the spread of germs, to remove ultrasound gel, etc.). The ultrasound probe 116 may be the only component of the neuromodulation system 10 to directly contact the patient's skin during treatment, and thus the only component that requires cleaning and disinfecting in between uses. That is, the operator may not need to clean and disinfect the positioner system 32 between each use. Accordingly, the operator may take a few minutes (e.g., 1-2 minutes, 1-5 minutes, 5-10 minutes) to clean and disinfect the ultrasound probe 116 and the subject's skin.

Therefore, the present embodiments may increase the effectiveness (e.g., due to proper and consistent probe placement and pressure) and reduce the complexity of administering neuromodulation treatments. For example, operators may not have to learn different techniques for identifying a region of interest and associated treatment position with the positioner system 32, as the positioner system 32 allows for free scanning before the ultrasound probe 116 is inserted into the probe holder 40. Further, the positioner system 32 may be operated by a single operator using a single hand, as rotating two knobs (e.g., positioner lock knob 206, compression adjustment knob 214) sequentially may secure the position of the ultrasound probe 116 (e.g., prevent movement between components of the positioner system 32) and apply pressure, and rotating a single knob of the two knobs (e.g., positioner lock knob 206) may release the pressure applied and allow movement between components of the system. Moreover, the worm gear system 212 of the pressure applicator 42 may allow for gradual and steady pressure application, thereby preventing or reducing large and sudden changes in applied pressure which may lead to patient discomfort. Additionally, the worm gear system 212 may prevent backlash between components of the positioner system 32 during pressure application and pressure release. The positioner system 32 may also reduce the time needed to set up and adjust the system to the subject's unique anatomy and clinical condition, as the positioner system 32 includes multiple degrees of freedom allowing for height adjustments, rotational adjustments, and the like. Additionally, the positioner system 32 may reduce the time in between treating patients, as the ultrasound probe 116 may be the only component of the neuromodulation system 10 to directly contact the subject's skin during treatment, and thus the only component that requires cleaning and disinfecting in between uses. Likewise, the positioner system 32 is not required to be machined out of biosafe and biocompatible materials, as it is not expected to contact the subject's skin, which may reduce the cost of manufacturing the positioner system 32. Accordingly, the presently disclosed techniques may improve the experience of both patients and operators (e.g., clinicians, sonographers, etc.) during neuromodulation treatments.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. An ultrasound probe positioner system, comprising:

a probe holder comprising a receptacle configured to receive an ultrasound probe;

a pressure applicator comprising:

a pivot arm configured to rotatably couple to the receptacle of the probe holder;

a first knob, wherein rotation of the first knob in a first direction is configured to prevent relative motion between the pivot arm and the receptacle of the probe holder; and a second knob, wherein rotation of the second knob is configured to adjustably apply pressure to the pivot arm and control an angular position of the pivot arm; and a slider arm comprising:

an arm; and a slide disposed on the arm, wherein the slide is configured to couple to the pressure applicator, and wherein a position of the slide is adjustable along a length of the arm.

2. The ultrasound probe positioner system of claim 1, wherein the slider arm comprises a mount configured to couple to a cart or mobile stand, wherein the cart or mobile stand is configured to support the slider arm above or near a subject.

3. The ultrasound probe positioner system of claim 1, wherein rotation of the first knob in the first direction is further configured to prevent motion of the slide along the slider arm.

4. The ultrasound probe positioner system of claim 1, wherein rotation of the first knob in a second direction is configured to allow relative motion between the pivot arm and the receptacle and allow motion of the slide along the slider arm.

5. The ultrasound probe positioner system of claim 4, wherein rotation of the first knob in the second direction is further configured to release pressure applied via rotation of the second knob.

6. The ultrasound probe positioner system of claim 1, wherein the receptacle of the probe holder comprises:

a lower receptacle comprising one or more walls, wherein the one or more walls are formed to substantially match a shape and curvature of at least a portion of the ultrasound probe to define a snap fit between the lower receptacle and the ultrasound probe; and an upper receptacle configured to rotatably couple to the pivot arm of the pressure applicator.

7. The ultrasound probe positioner system of claim 6, wherein an internal surface of the upper receptacle comprises a set of teeth configured to interface with a complementary set of teeth on a surface of the lower receptacle to removably mate the upper receptacle and the lower receptacle.

8. The ultrasound probe positioner system of claim 7, wherein a gap between the set of teeth and the complementary set of teeth is configured to allow rotational movement between the upper receptacle and the lower receptacle, and wherein applying pressure to the pivot arm via rotation of the second knob is configured to close the gap and prevent rotational movement between the upper receptacle and the lower receptacle.

9. The ultrasound probe positioner system of claim 1, wherein the arm comprises a substantially hexagonal cross section to prevent free radial rotation of the slider arm.

10. The ultrasound probe positioner system of claim 9, wherein an angular position of the pressure applicator is adjustable to one of a number of fixed angles defined by a respective side of the arm.

11. The ultrasound probe positioner system of claim 1, wherein the slider arm comprises a cord management feature integrated into an end of the arm, wherein the cord management feature is configured to accommodate a cord of the ultrasound probe.

12. The ultrasound probe positioner system of claim 1, wherein the pressure applicator comprises a worm gear system controlled via rotation of the first knob and rotation of the second knob, wherein rotation of the second knob is configured to control an amount of pressure applied via the worm gear system, and wherein rotation of the first knob is configured to release the pressure applied via the worm gear system.

13. The ultrasound probe positioner system of claim 1, wherein the ultrasound probe positioner system comprises six points of articulation.

* * * * *